United States Patent
Song et al.

(10) Patent No.: US 10,088,540 B2
(45) Date of Patent: Oct. 2, 2018

(54) METHOD FOR IDENTIFYING CHEMICAL SPECIES IN A SUBSTANCE USING NQR

(71) Applicant: SCHLUMBERGER TECHNOLOGY CORPORATION, Sugar Land, TX (US)

(72) Inventors: Yi-Qiao Song, Newton Center, MA (US); Soumyajit Mandal, Cleveland, OH (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 293 days.

(21) Appl. No.: 14/888,732

(22) PCT Filed: May 1, 2014

(86) PCT No.: PCT/US2014/036286
§ 371 (c)(1),
(2) Date: Nov. 3, 2015

(87) PCT Pub. No.: WO2014/179521
PCT Pub. Date: Nov. 6, 2014

(65) Prior Publication Data
US 2016/0077178 A1    Mar. 17, 2016

Related U.S. Application Data
(60) Provisional application No. 61/819,374, filed on May 3, 2013.

(51) Int. Cl.
*G01V 3/00* (2006.01)
*G01R 33/44* (2006.01)
*G01N 24/08* (2006.01)

(52) U.S. Cl.
CPC ........ *G01R 33/441* (2013.01); *G01N 24/081* (2013.01); *G01N 24/084* (2013.01)

(58) Field of Classification Search
USPC ....................................................... 324/309
See application file for complete search history.

(56) References Cited

U.S. PATENT DOCUMENTS

| | | | | |
|---|---|---|---|---|
| 3,711,764 A | * | 1/1973 | Ernst | G01R 33/389 324/310 |
| 6,100,688 A | * | 8/2000 | Smith | G01R 33/381 324/300 |

(Continued)

FOREIGN PATENT DOCUMENTS

| | | |
|---|---|---|
| WO | WO9221987 A1 | 12/1992 |
| WO | WO9516926 A1 | 6/1995 |
| WO | WO2013134474 A1 | 9/2013 |

OTHER PUBLICATIONS

Pound, R. V., "Nuclear Electric Quadrupole Interactions in Crystals", Physical Review, 1950, 79(4), pp. 685-705.

(Continued)

*Primary Examiner* — Rodney Fuller

(57) ABSTRACT

Methods and systems for identifying a chemical species within a substance using nuclear quadrupole resonance (NQR) are described herein. One method includes applying a number of NQR perturbation-detection pulse sequences to the substance. Each perturbation-detection pulse sequence includes a perturbation segment applied at a perturbation frequency and a detection segment applied at a second different frequency. As the sequences are applied, the perturbation frequency, the second frequency, or both are varied for each pulse sequence. The method also includes applying a number of NQR reference pulse sequences to the substance at a reference frequency. The reference frequency is varied for each pulse sequence. A chemical species is (Continued)

identified within the substance by comparing (i) a set of NQR signals generated by the perturbation-detection pulse sequences with (ii) a reference set of NQR signals generated by the reference pulse sequences.

20 Claims, 13 Drawing Sheets

(56) References Cited

U.S. PATENT DOCUMENTS

| | | | |
|---|---|---|---|
| 7,999,541 | B2 | 8/2011 | Chisholm et al. |
| 9,632,203 | B2 | 4/2017 | Hopper et al. |
| 9,851,420 | B2 | 12/2017 | Song |
| 9,927,550 | B2 | 3/2018 | Mandal et al. |
| 2006/0226838 | A1 | 10/2006 | Smith et al. |
| 2009/0039884 | A1* | 2/2009 | Schiano ............ G01R 33/441 |
| | | | 324/307 |
| 2011/0018535 | A1 | 1/2011 | Rudakov |
| 2012/0001629 | A1 | 1/2012 | Hopper et al. |
| 2013/0234705 | A1 | 9/2013 | Mandal et al. |
| 2015/0077102 | A1* | 3/2015 | Mandal ............ G01N 24/084 |
| | | | 324/303 |

OTHER PUBLICATIONS

Dehmelt, H. G., "Nuclear Quadrupole Resonance", America Journal of Physics, 1954, 22(3), pp. 110-120.

Garroway, A. N. et al., "Remote Sensing by Nuclear Quadrupole Resonance", Geoscience and Remote Sensing, IEEE Transactions on, 2001, 39(6), pp. 1108-1118.

Lee, Y. K., "Spin-1 Nuclear Quadrupole Resonance Theory with Comparisons to Nuclear Magnetic Resonance", Concepts in Magnetic Resonance Part A, 2002, 14(3), pp. 155-171.

Ostroff, E. D. et al., "Multiple Spin Echoes and Spin Locking in Solids", Physical Review Letters, 1966. 16(24), pp. 1097-1099.

Marino, R. A. et al., "Multiple Spin Echoes in Pure Quadrupole Resonance", The Journal of Chemical Physics, 1977, 67(7), pp. 3388-3389.

Cantor, R.S. et al., "Pulsed Spin Locking in Pure Nuclear Quadrupole Resonance", The Journal of Chemical Physics, 1980, 73(3), pp. 1054-1063.

Luznik, J. et al., "Zeeman Shift—A Tool for Assignment of 14N NQR Lines of Nonequivalent 14N Atoms in Powder Samples", Journal of Magnetic Resonance, 2011, 212(1), pp. 149-153.

Sauer, K. L. et al., "Spin Dynamics in the Pulsed Spin Locking of Nuclear Quadrupole Resonance", Physical Review B, 2006, 74(17), pp. 174410.

Slusher, R. E. et al., "Sensitive Detection of Nuclear Quadrupole Interactions in Solids", Physical Review, 1968, 166 (2), pp. 332-347.

Search Report and Written Opinion of International Application No. PCT/US2014/036286 dated Jan. 28, 2016, 9 pages.

Kerogen (Dec. 9, 2017). In Wikipedia. Retrieved Jan. 15, 2018, from https://en.wikipedia.org/wiki/Kerogen.

* cited by examiner

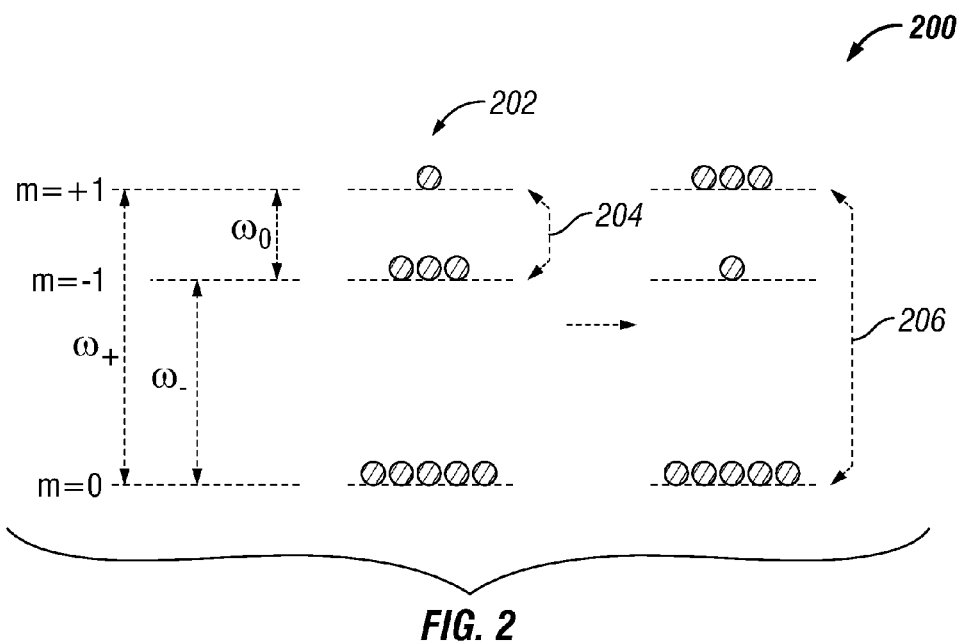
FIG. 2
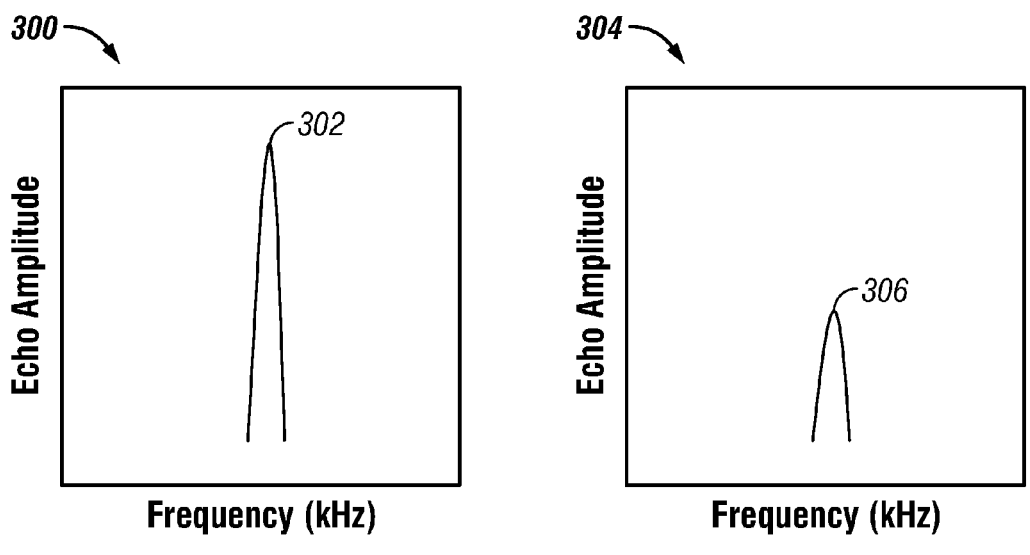
FIG. 3A  FIG. 3B

METHOD FOR IDENTIFYING CHEMICAL SPECIES IN A SUBSTANCE USING NQR

PRIORITY

The present application claims the benefit of U.S. Application Ser. No. 61/819,374, filed May 3, 2013, which application is incorporated herein, in its entirety, by reference.

TECHNICAL FIELD

This disclosure relates to nuclear quadrupole resonance (NQR) and, more particularly, to using nuclear quadrupole resonance (NQR) for determining properties of substances.

BACKGROUND

Nuclear quadrupole resonance (NQR) is a phenomenon where certain atomic nuclei generate resonant signals when an oscillating magnetic field at a particular frequency is applied to the nuclei. Some atomic nuclei can generate resonant signals responsive to two or more different applied frequencies. The NQR resonant signals can be detected without an externally applied magnetic field. Different atomic nuclei will have different resonant frequencies. For example, the resonant frequencies of nitrogen are different from the resonant frequencies of chlorine. Also, atomic nuclei of the same chemical element that are located within different chemical species can have different resonant frequencies. For example, the nitrogen nuclei located within the ammonium nitrate will have different resonant frequencies from nitrogen nuclei located within RDX. Furthermore, atomic nuclei of the same chemical element that are located within different sites of a chemical species can also have different resonant frequencies. Such NQR phenomena can be used to determine properties of a substance.

SUMMARY

Illustrative embodiments of the present disclosure are directed to a method for identifying chemical species within a substance using nuclear quadrupole resonance (NQR). The method includes applying a number of NQR perturbation-detection pulse sequences to the substance. Each perturbation-detection pulse sequence includes a perturbation segment applied at a perturbation frequency and a detection segment applied at a second different frequency. As the sequences are applied, the perturbation frequency, the second frequency, or both are varied for each pulse sequence. The method also includes applying a number of NQR reference pulse sequences to the substance. Each reference pulse sequence is applied at a reference frequency, which is varied for each pulse sequence. A perturbation-detection set of NQR signals are generated within the substance by each of the perturbation-detection pulse sequences. The perturbation-detection set of NQR signals is detected. Also, a reference set of NQR signals generated within the substance by each of the reference pulse sequences is detected. A chemical species is identified within the substance by comparing the perturbation-detection set of NQR signals and the reference set of NQR signals.

In various embodiments, identifying the chemical species within the substance includes using the set of perturbation-detection NQR signals to generate a two-dimensional spectrum of the perturbation frequency versus the second frequency and using the reference set of NQR signals to generate a reference spectrum for the reference frequency. The two-dimensional spectrum is compared to the reference spectrum to identify the chemical species within the substance.

In some embodiments, comparing the two-dimensional spectrum to the reference spectrum includes generating a difference spectrum using the two-dimensional spectrum and the reference spectrum. Peaks are identified within the difference spectrum. The particular frequencies associated with these peaks can be used to identify the chemical species within the substance.

Various embodiments are also directed to a NQR system for identifying chemical species within a substance. The system includes one or more coils for applying NQR pulse sequences to a substance and for detecting NQR signals generated within the substance. A NQR transmitter is electronically coupled to the coil and generates NQR pulse sequences that are transmitted to the coil. A NQR receiver is coupled to the coil and processes detected NQR signals. The system also includes a processor and a memory that stores instructions executable by the processor to perform various processes. The processes include providing a number of NQR perturbation-detection pulse sequences to the NQR transmitter. Each perturbation-detection pulse sequence includes a perturbation segment at a perturbation frequency and a detection segment at a second different frequency. The perturbation frequency, the second frequency, or both are varied for each pulse sequence. The processes also include providing a number of NQR reference pulse sequences to the NQR transmitter. The reference pulse sequences are applied at a reference frequency that is varied for each pulse sequence. The processes further include receiving (i) a perturbation-detection set of NQR signals generated within the substance by each of the perturbation-detection pulse sequences and (ii) a reference set of NQR signals generated within the substance by each of the reference pulse sequences. A chemical species is identified within the substance by comparing the perturbation-detection set of NQR signals and the reference set of NQR signals.

BRIEF DESCRIPTION OF THE DRAWINGS

Further features and advantages will become more readily apparent from the following detailed description when taken in conjunction with the accompanying drawings:

FIG. 2 shows an energy-level diagram for atomic nuclei with a spin quantum number equal to 1 in accordance with one embodiment of the present disclosure;

FIG. 3A shows a first peak in a detected resonant signal in accordance with one embodiment of the present disclosure;

FIG. 3B shows a second peak in a detected resonant signal in accordance with one embodiment of the present disclosure;

DETAILED DESCRIPTION

Illustrative embodiments are directed to methods and systems for identifying chemical species within an unknown substance using nuclear quadrupole resonance (NQR). One method includes applying a number of NQR perturbation-detection pulse sequences to the substance. Each perturbation-detection pulse sequence includes a perturbation segment applied at a perturbation frequency and a detection segment applied at a second different frequency. As the sequences are applied, the perturbation frequency, the second frequency, or both are varied for each pulse sequence. The method also includes applying a number of NQR reference pulse sequences to the substance. The reference pulse sequences are applied at a reference frequency that is varied for each pulse sequence. A perturbation-detection set of NQR signals is generated within the substance by each of the perturbation-detection pulse sequences. The perturbation-detection set of NQR signals are detected. Also, a reference set of NQR signals generated within the substance by each of the reference pulse sequences is detected. A chemical species is identified within the substance by comparing the perturbation-detection set of NQR signals and the reference set of NQR signals. In this manner, some embodiments of the present disclosure "scan" across many different NQR frequencies to efficiently and accurately identify chemical species within an unknown sample. Details of illustrative embodiments are described below.

Figure 1A:
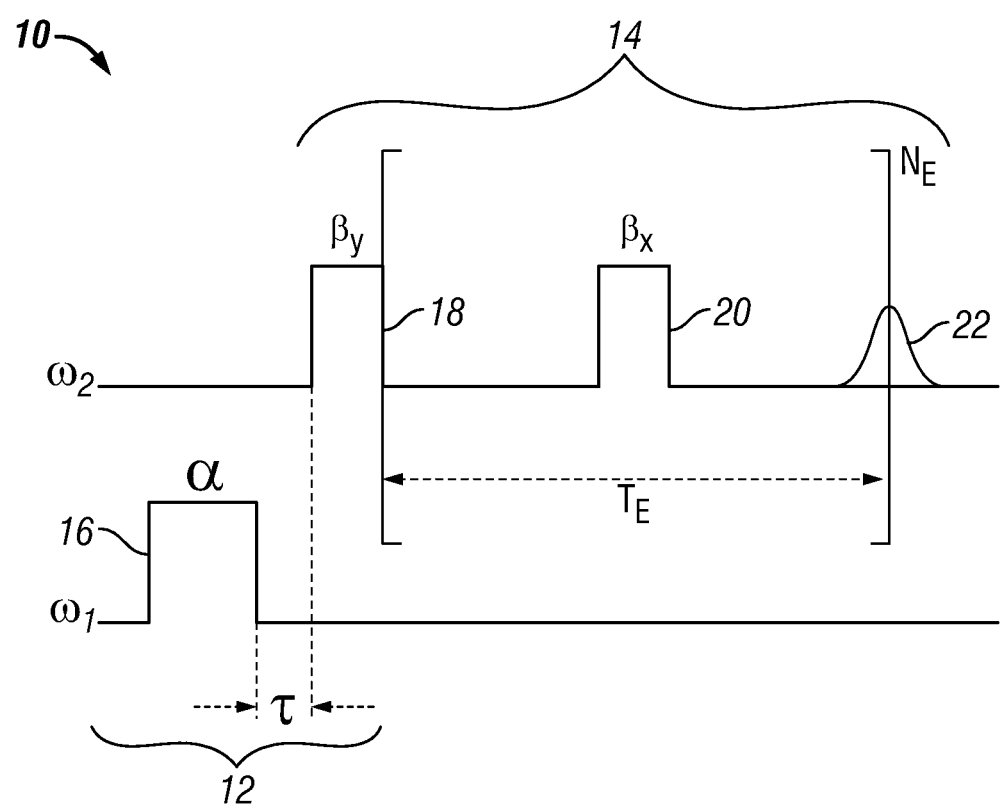
FIG. 1A shows a nuclear quadrupole resonance (NQR) perturbation-detection sequence in accordance with one embodiment of the present disclosure.

Various embodiments of the present disclosure use NQR pulse sequences with perturbation segments. The perturbation segments can be used to improve the accuracy of NQR measurements and determinations. FIG. 1A shows a NQR perturbation-detection sequence 10 in accordance with one embodiment of the present disclosure. The perturbation-detection sequence includes a perturbation segment 12 followed by a detection segment 14. The perturbation segment 12 is applied at a perturbation frequency ($\omega_1$) and the detection segment 14 is applied at a second frequency ($\omega_2$). The perturbation frequency may match a known resonant frequency of a set of atomic nuclei at a site within a chemical species (e.g., 737 kHz for glycine), while the second frequency may match a known resonant frequency of the set of atomic nuclei at the same site within the chemical species (e.g., 1052 kHz for glycine). In the specific example of FIG. 1A, the perturbation segment 12 includes a single pulse 16 with a nutation angle of $\alpha$. In some embodiments, the nutation angle can vary between 90 degrees and 180 degrees. The detection segment 14 includes an excitation pulse 18 followed by a number ($N_E$) of refocusing pulses 20 and corresponding echoes 22. In specific embodiments, the detection segment 14 is one of a spin-locked spin echo (SLSE) sequence or a steady-state free precession (SSFP) sequence. A time interval of $\tau$ is located between the perturbation segment 12 and the detection segment 14. In one example, the time interval is selected to avoid relaxation of the atomic nuclei of interest. In a specific example, the time interval is selected to be less than or equal to the $T_1$ relaxation time of the atomic nuclei of interest, which is a function of the frequency of the perturbation segment ($\omega_1$) 12 (e.g., $\tau=T_1(\omega_1)$).

In various embodiments of the present disclosure, the NQR perturbation-detection sequence 10 can improve the accuracy of NQR measurements and determinations by modulating the populations of energy levels of atomic nuclei at a particular site within a chemical species. FIG. 2 shows an energy-level diagram 200 in accordance with one embodiment of the present disclosure. In particular, the energy-level diagram 200 represents energy states for atomic nuclei with a spin quantum number (I) equal to 1. For this reason, in this case, the energy level diagram includes three levels, corresponding to the spin values of $\{-I,-I+1, \ldots +I\}$ allowed by quantum mechanics, i.e., $\{-1, 0,$ and $1\}$. A NQR transition (also known as a line or resonance) is caused by the nucleus jumping between a pair of these levels. There are three possible pairs, which results in three NQR transitions commonly denoted by $\omega_+$, $\omega_-$, and $\omega_0$. At thermal equilibrium 202, each energy level includes a certain population of atomic nuclei. In some cases, the perturbation frequency of the perturbation segment ($\omega_1$) 204 may match a known resonant frequency ($\omega_0$) of atomic nuclei transitions between two energy levels. When this perturbation segment 204 is applied to the substance, the atomic nuclei transition between the +1 and −1 energy levels. As a result, the populations of the +1 and −1 energy levels are inverted before a detection segment 206 is applied. The detection segment ($\omega_2$) 206 may match another known resonant frequency ($\omega_+$) of the atomic nuclei. The resonant signal generated by the perturbation segment 204 and the detect segment 206 are detected by the NQR system. As shown in FIG. 2, the perturbation segment 204 causes a change within the population of the +1 energy level. In particular, the population of the +1 energy level is now increased to three atomic nuclei. This change in population is detected by applying the detection segment 206 to the substance and detecting a resonant signal with decreased amplitude. The signal has decreased amplitude because the difference between populations between level +1 and level 0 is smaller, as compared with the difference at thermal equilibrium 202. In this manner, various embodiments of the present disclosure can detect the presence of one NQR transition (e.g., at $\omega_1$) by observing signals produced by another transition (e.g., at $\omega_2$).

In various embodiments of the present disclosure, the NQR perturbation-detection sequences can be used with other NQR sequences to improve the accuracy of NQR measurements and determinations by identifying the presence of a particular atomic nuclei of interest. For example, a reference NQR pulse sequence, such as an SLSE sequence, is applied to a substance with a frequency ($\omega_1$). The frequency ($\omega_1$) may match a known resonant frequency ($\omega_0$) of a set of atomic nuclei of interest within a chemical species. A reference resonant signal produced by the reference sequence is detected. FIG. 3A shows a plot 300 of echo amplitude versus frequency in accordance with one embodiment of the present disclosure. The plot 300 shows a first peak 302 within the detected resonant signal for the reference NQR pulse sequence. A second NQR pulse sequence is applied to the substance. The second NQR pulse sequence is a perturbation-detection sequence as shown in, for example, FIG. 1A. The frequency of the perturbation segment ($\omega_1$) matches the known resonant frequency ($\omega_0$) of the set of atomic nuclei and the detection segment ($\omega_2$) may match another known resonant frequency ($\omega_+$) of the atomic nuclei. The resonant signal generated by the perturbation segment and the detection segment are detected by the NQR system. FIG. 3B shows a plot 304 of echo amplitude versus frequency in accordance with one embodiment of the present disclosure. The plot 304 shows a second peak 306 within the detected resonant signal for the NQR perturbation-detection sequence. As compared with FIG. 3A, the amplitude for the second peak 306 is smaller than the first peak 302 produced by the reference sequence. This decrease in amplitude confirms that the first peak 302 is representative of the set of atomic nuclei of interest within the particular chemical species. If the first peak 302 was generated by outside noise and/or by a different chemical species within the substance, then there would likely be no change in the amplitude of the first peak. In this manner, various embodiments of the perturbation-detection sequence can reduce false-positives and can more accurately identify specific chemical species, such as TNT (2,4,6-trinitrotoluene) and RDX (hexahydro-1,3,5-trinitro-1,3,5-triazine) within the substance.

Illustrative embodiments of the present disclosure are not limited to using $\omega_0$ as the perturbation frequency ($\omega_1$) and $\omega_+$ as the second frequency ($\omega_2$). Many different combinations of known resonant frequencies (e.g., $\omega_0$, $\omega_+$, and $\omega_-$) can achieve similar results. For example, in some cases, the resonant frequencies may produce a resonant signal with amplitude that increases, as compared with the reference resonant signal. Table 1 below shows amplitude changes for various known resonant frequencies.

TABLE 1

| | $\omega_2 = \omega_+$ | $\omega_2 = \omega_-$ | $\omega_2 = \omega_0$ |
|---|---|---|---|
| $\omega_1 = \omega_+$ | | Decrease | Decrease |
| $\omega_1 = \omega_-$ | Decrease | | Increase |
| $\omega_1 = \omega_0$ | Decrease | Increase | |

The perturbation-detection sequences and methods described above can be applied to a substance in order to identify particular chemical species within the substance. Various embodiments described herein are directed to a method that identifies chemical species within the substance (e.g., sample) when the chemical species within the substance are unknown. Details of this method are further described below.

Figure 4:
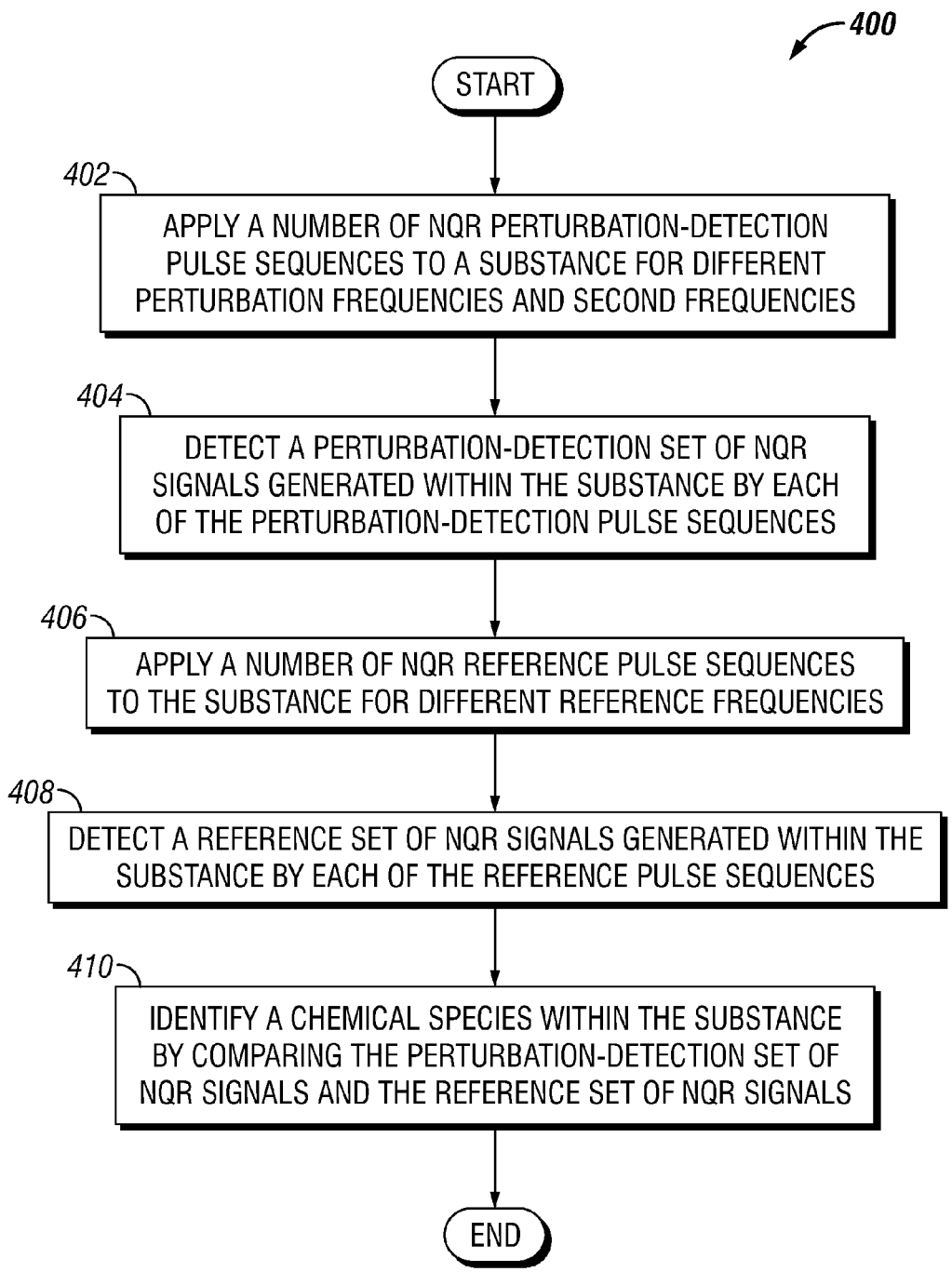
FIG. 4 shows a method for identifying chemical species within a substance using NQR in accordance with one embodiment of the present disclosure.

FIG. 4 shows a method 400 for identifying chemical species within a substance using NQR. At process 402, the method includes applying a number of NQR perturbation-detection pulse sequences to the substance. Each perturbation-detection pulse sequence includes a perturbation segment applied at a perturbation frequency and a detection segment applied at a second frequency. The detection segment can be a SLSE or a SSFP sequence. The perturbation frequency, the second frequency, or both are varied for each pulse sequence. The perturbation frequency and the second frequency are applied at different frequencies. At process 404, a perturbation-detection set of NQR signals is detected. The perturbation-detection set of NQR signals is generated within the substance by each of the perturbation-detection pulse sequences. Processes 402 and 404 can be performed in the following manner to scan across a range of different frequencies.

Sub-process (A)—Set the perturbation frequency ($\omega_1$) for the perturbation segment, set the second frequency ($\omega_2$) for the detection segment, and apply the perturbation-detection sequence to the substance to detect and obtain a NQR signal.

Sub-process (B)—Change $\omega_2$ to a different frequency, maintain $\omega_1$, and apply the perturbation-detection sequence to the substance to detect and obtain another NQR signal.

Sub-process (C)—Repeat sub-process (B) in order to scan many frequencies that span a range of frequencies to determine a NQR spectrum based on a set of detected NQR signals. The method obtains the NQR spectrum for a range of different $\omega_2$ values. For example, the value of $\omega_2$ could be varied over a range of 700 kHz to 1100 kHz in 10 kHz intervals, resulting in 41 different frequencies. This spectrum is referred to as $S_1(\omega_2)$.

Sub-process (D)—Change the perturbation frequency ($\omega_1$) to a different value, repeat sub-processes (A)-(C) to obtain a NQR spectrum with $\omega_1$ set at this new value. The new spectrum is referred to as $S_2(\omega_2)$.

Sub-process (E)—Repeat sub-process (D) to obtain the spectrum for many values of $\omega_1$. For example, the value of $\omega_1$ could be varied over a range of 700 kHz to 1100 kHz in 10 kHz intervals, resulting in 41 different frequencies. The result is a two-dimensional spectrum (or array) of data points as a function of $\omega_1$ and $\omega_2$. This two-dimensional NQR spectrum is referred to as $S(\omega_1, \omega_2)$.

At process 406, the method includes applying a number of NQR reference pulse sequences to the substance. The reference pulse sequences are applied at a reference frequency that is varied for each pulse sequence. In some embodiments, the reference pulse sequence is a SLSE or a SSFP sequence without a perturbation segment. At process 408, a reference set of NQR signals is detected. The reference set of NQR signals is generated within the substance by each of the reference pulse sequences. The reference set of NQR signals are obtained without using a perturbation-detection sequence. In some embodiments, the reference frequency is varied over the same set of frequencies as the second frequency in the perturbation-detection sequence. Processes 406 and 408 can be performed in the following manner to scan across a range of different reference frequencies.

Sub-process (F)—Set the reference frequency ($\omega_3$) (e.g., to correspond with $\omega_2$) and apply the reference sequence to the substance to detect and obtain a reference NQR signal.

Sub-process (G)—Change $\omega_3$ to a different frequency (e.g., that corresponds to $\omega_2$) and apply the reference sequence to the substance to detect and obtain another reference NQR signal.

Sub-process (H)—Repeat sub-process (G) in order to scan many reference frequencies to determine a one-dimensional reference spectrum based on a set of reference NQR signals. In this manner, the method obtains a one-dimensional reference spectrum for a range of different reference frequencies. In some embodiments, the reference frequencies correspond with the second frequencies used in the detection segment of the perturbation-detection sequences in processes 402 and 404. In cases where $\omega_3$ corresponds to $\omega_2$, the one-dimensional reference spectrum is referred to herein as $S_0(\omega_2)$.

Figure 1B:
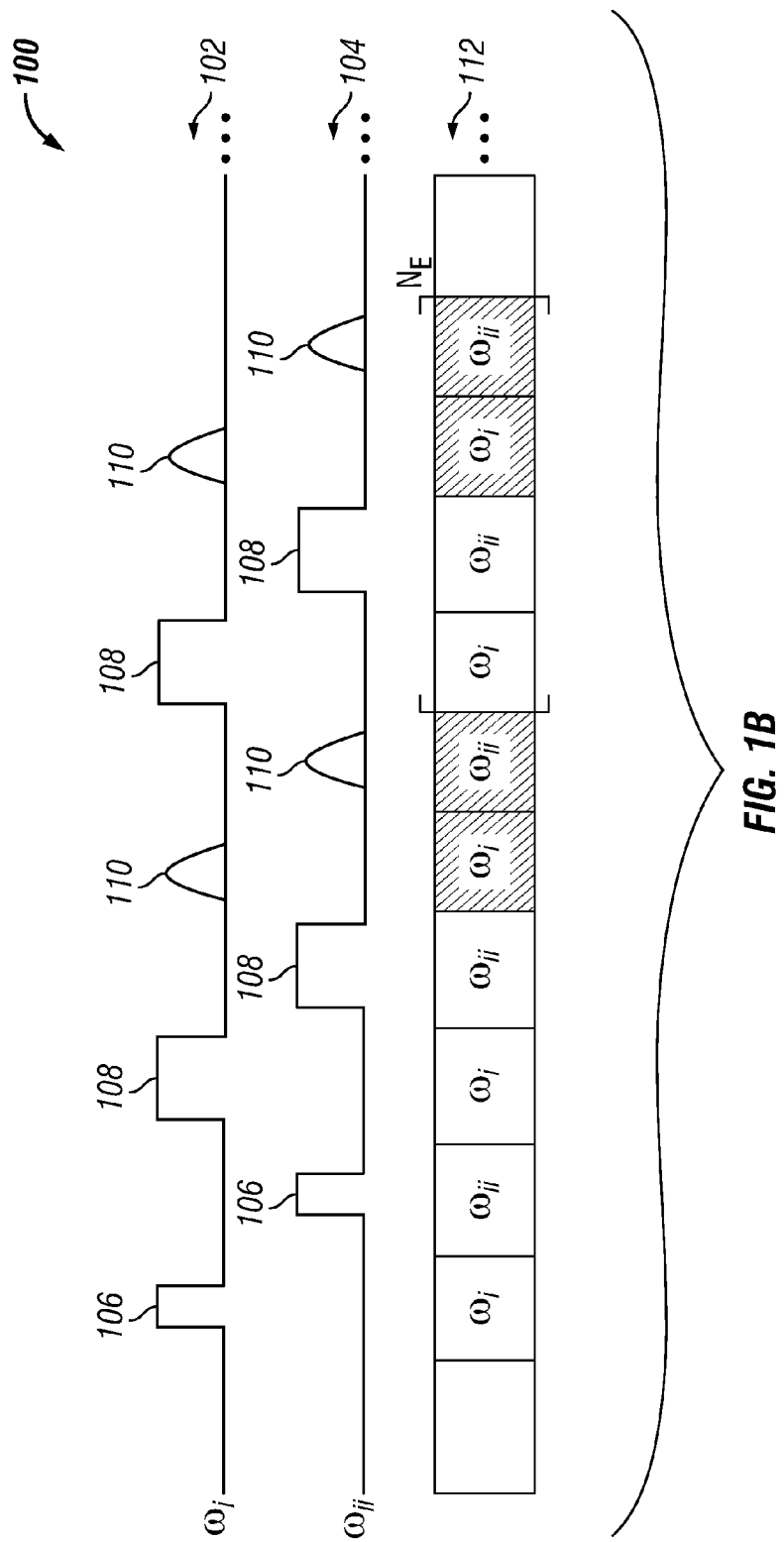
FIG. 1B shows interposed NQR pulse sequences in accordance with one embodiment of the present disclosure.

The perturbation-detection sequences and reference sequences described herein can be more efficiently applied by interposing sequences within one another. For example, in some embodiments, at least one NQR perturbation-detection pulse sequence is at least partially interposed within another perturbation-detection sequence. In this manner, NQR measurements can be performed in parallel to more efficiently make measurements, whereas in many conventional systems, the measurements are performed in series. FIG. 1B shows interposed pulse sequences in accordance with one embodiment of the present disclosure. The figure shows a first pulse sequence 102 and a second pulse sequence 104. Each sequence includes an excitation pulse 106, a series of refocusing pulses 108, and a series of echoes 110. In one specific example, the sequences 102, 104 are SLSE sequences. In other embodiments, the sequences are 102, 104 are SSFP sequences. In further embodiments, the sequences 102, 104 are perturbation-detection sequences, as shown in for example FIG. 1A. The sequences 102, 104 can also be any combination of different NQR sequences (e.g., SLSE, SSFP and/or perturbation-detect sequences).

As shown in FIG. 1B, the second sequence 104 is at least partially interposed within the first sequence 102. In other words, at least one pulse or detected echo of the second sequence 104 occurs before the first pulse sequence 102 is completed. The first sequence 102 is applied to the substance with a first set of frequencies ($\omega_i$) and the second sequence 104 is applied to the substance with a second set of frequencies ($\omega_{ii}$). The frequency difference ($\Delta\omega_0$) between the two sets of frequencies or even frequencies within the same set can be as great as 10%. In various other embodiments, the frequency can be even greater (e.g., 20% 30% or 50%).

In various embodiments of the present disclosure, the first sequence 102 may match at least one resonant frequency of a first set of atomic nuclei (e.g., a first site of nitrogen in TNT at 842 kHz) and the second segment 104 may match at least one resonant frequency of a second set of atomic nuclei (e.g., a second site of nitrogen in TNT at 768 kHz). In this manner, the first sequence 102 generates a first resonant signal in the first set of nuclei and the second sequence 104 generates a second resonant signal in the second set of nuclei.

In a specific example, the interposed pulse sequences are perturbation-detection sequences. In such an embodiment, the sequences 102, 104 may include four different frequencies. The first sequence 102 includes a first perturbation frequency for the perturbation segment and a second frequency for the detection segment, while the second sequence 104 includes a third perturbation frequency for the perturbation segment and a fourth frequency for the detection segment. In another example, if four perturbation-detection sequences are applied, then the entire resulting sequence may include eight different frequencies.

The interposed pulse sequences (e.g., perturbation-detection or reference sequences) can be applied using a non-resonant transmitter, such as the non-resonant transmitter described below. Further details regarding interposed sequences can be found in U.S. Publication No. 2012/0001629 published on Jan. 5, 2012, and PCT Publication No. WO 2013/134474, published on Sep. 12, 2013. Both of these references are incorporated herein, in their entireties, by reference.

Referring back to FIG. 4, at process 410, a chemical species is identified within the substance by comparing the perturbation-detection set of NQR signals and the reference set of NQR signals. For example, a chemical species can be identified by comparing the $S(\omega_1, \omega_2)$ and $S_0(\omega_2)$ spectrums. In particular, the echo amplitudes can be compared between the two different spectrums. For example, consider a single compound with three NQR transitions. The two-dimensional NQR spectrum for the system will be compared with $S_0(\omega_2)$ for each $\omega_1$ value (which is a line in the $S(\omega_1, \omega_2)$ array). If the echo amplitude for $S(\omega_1, \omega_2)$ is larger than the echo amplitude $S_0(\omega_2)$ at the $\omega_2$ value, then an increase ("+") is identified for that pair of ($\omega_1, \omega_2$). Similarly, if the echo amplitude is smaller, then a decrease is identified ("−") for that pair. Such an analysis could be described mathematically as a difference spectrum. Equation 1 below can be used to determine a difference spectrum:

$$S_d(\omega_1,\omega_2)=\text{sign}[S(\omega_1,\omega_2)-S_0(\omega_2)] \qquad (1)$$

Equation 2 below can be used to determine a normalized difference spectrum:

$$S_d(\omega_1,\omega_2)=S(\omega_1,\omega_2)/S_0(\omega_2)-1 \qquad (2)$$

A threshold can also be applied to the difference spectrum at an appropriate level in order to identify coupling between NQR lines. Differences between $S(\omega_1,\omega_2)$ and $S_0(\omega_2)$ that are smaller than the threshold are ignored, i.e., the corresponding values in the difference spectrum $S_d(\omega_1,\omega_2)$ are set to zero. The value of this threshold is designed to be high enough to remove random differences between $S(\omega_1,\omega_2)$ and $S_0(\omega_2)$ due to noise, but low enough to allow systematic differences due to coupling between NQR lines to be retained and easily identified.

The positive and negative peaks within the difference spectrum can then be used to identify a chemical species by comparing the frequencies associated with the positive and negative peaks with the spectral lines of the chemical species, such as those chemical species shown in Table 2 below.

Figure 5A:
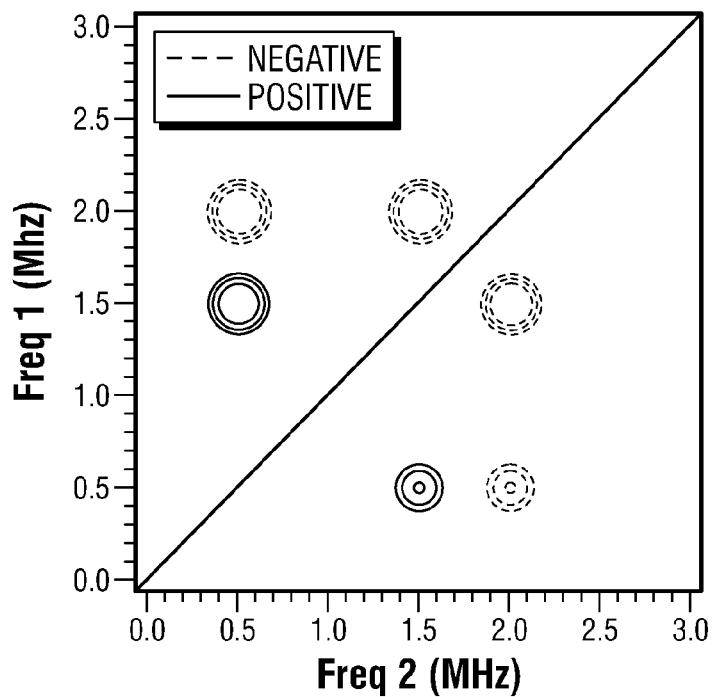
FIGS. 5A and 5B show a two-dimensional difference spectrum in accordance with one embodiment of the present disclosure.
Figure 5B:
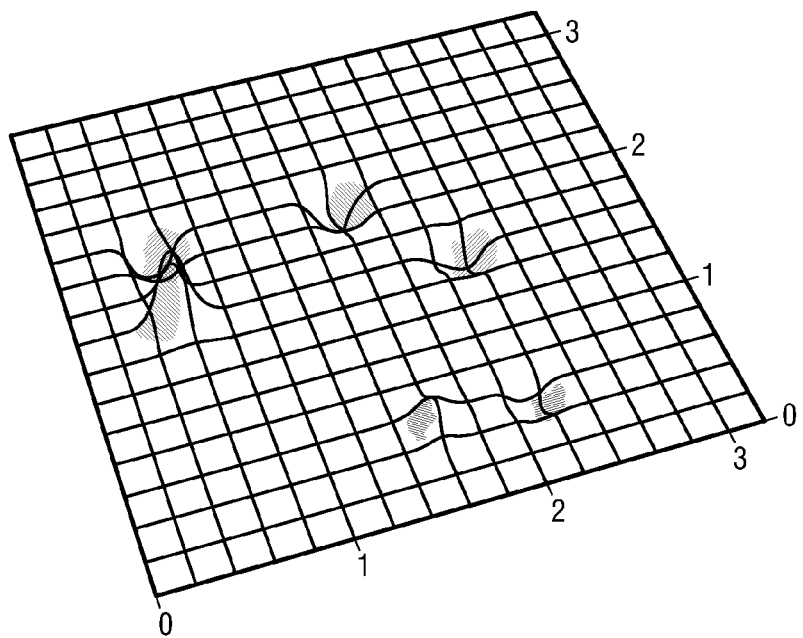

FIGS. 5A and 5B show a two-dimensional NQR difference spectrum for an atomic nucleus site within a chemical compound. FIG. 5A shows an example of a two-dimensional contour map of the difference signal (such as $S_d(\omega_1, \omega_2)$) measured by the method described above. The dashed contours represent a negative signal (e.g., a decrease) and the solid contours represent a positive signal (e.g., an increase). The signal near the center line ($\omega_1=\omega_2$) is not acquired because it does not probe the interaction between different peaks. Other forms of the two-dimensional map can also be used, such as a surface plot, as shown in FIG. 5B. In the example of FIGS. 5A and 5B, the resonant frequencies correspond to $\omega_0/2\pi=0.5$ MHz, $\omega_+/2\pi=2$ MHz, and $\omega_-/2\pi=1.5$ MHz. The two-dimensional difference spectrum shows that the associated three transitions (peaks) are due to the same atomic nucleus site within the chemical compound. For a mixture with multiple chemical compounds (e.g.

multiple crystalline sites), the two-dimensional difference spectrum will be a superposition of several of these patterns. Analyzing these patterns will allow the determination of the corresponding atomic nucleus site and chemical species.

Sub-processes (A)-(H) described above are not limited to this particular order. For example, in another embodiment, sub-processes (F)-(H) can take place before sub-processes (A)-(E). In other words, processes 406 and 408 can take place before processes 402 and 404. To this end, in various embodiments, the reference spectrum generated using the reference frequencies ($\omega_3$) can be used to inform selection of the perturbation frequency associated with the perturbation segment and the second frequency associated with the detection segment. For example, a number of NQR reference pulse sequences are applied to the substance. Each reference pulse sequence is applied at a reference frequency that is varied for each pulse sequence. A reference set of NQR signals generated within the substance by each of the reference pulse sequences is detected. The NQR signals generated within the substance by the series of NQR pulse sequences are detected and used to generate a one-dimensional reference spectrum for the first frequency. A number of peaks are identified within the one-dimensional reference spectrum. Then, the perturbation-detection pulse sequences are applied to the substance. The perturbation frequency and the second frequency within the perturbation-detection pulse sequences can be selected to match frequencies associated with the identified peaks in the reference spectrum (e.g., $\omega_a$, $\omega_b$, $\omega_c$). Thus, each perturbation-detection pulse sequence includes a perturbation frequency associated with one of the identified peaks and a detection segment associated with one of the identified peaks (e.g., a first pulse sequence using $\omega_b$ and $\omega_a$, a second pulse sequence using $\omega_c$ and $\omega_a$, a third pulse sequence using $\omega_a$ and $\omega_b$, a fourth pulse sequence using $\omega_c$ and $\omega_b$, and . . . ).

The NQR signals generated within the substance by the perturbation-detection pulse sequences are detected and chemical species within the substance can be identified using the detected NQR signals. If a particular perturbation-detection pulse sequence produces a decrease or an increase in amplitude for an identified peak, then the frequencies (e.g., lines) for that particular sequence are coupled. For example, if a pulse sequence includes a perturbation segment with a frequency of $\omega_a$ and a detection segment with a frequency of $\omega_b$, and the amplitude of the resonant signal produced by this pulse sequence is larger than the initial amplitude at $\omega_b$, then the $\omega_a$ and the $\omega_b$ lines are coupled and this coupling can be used to identify a site within the chemical species.

In one specific example, coupling between three NQR lines was determined by running SLSE experiments for possible pairs of lines, and comparing the resultant amplitudes with a reference case (e.g., perturbation pulse switched off). This approach is faster than running a full two-dimensional scan because a smaller set of experiments can be performed (e.g., a total of six SLSE experiments on the three lines). In general, this approach performs N(N-1) SLSE experiments on N lines.

The methods described herein can be used to identify various different chemical species. The chemical species can be a single chemical element, such as nitrogen, chlorine, potassium, and copper, or a chemical compound that includes any one of those atomic nuclei, such as glycine, ammonium nitrate, TNT (2,4,6-trinitrotoluene), RDX (hexahydro-1,3,5-trinitro-1,3,5-triazine), cocaine hydro-chloride, and/or heroin hydro-chloride (3,6-diacetoxy-7,8-dehydro-4,5-epoxy-N-methylmorphinan hydrochloride monohydrate). Table 2 shows the spectral lines for nitrogen, potassium, and chlorine at each site within several chemical species. The column headings are described below.

"Chemical Species" is a particular chemical species of interest;

"Site #" is a position of an atomic nucleus within a particular chemical species;

"Type" is an atomic nucleus at a site (e.g., chemical element and isotope);

"Weight %" is a contribution of a site to a total weight of a molecule of a chemical species;

"QCC" is a quadrupole coupling constant for a site;

"η" is a symmetry parameter for a site;

"NQR Frequency" is a known resonant frequency of an atomic nucleus within a site within a chemical species;

"FWHM" is an NQR line width for a particular NQR frequency (full-width at half-maximum);

"$T_1$" is a $T_1$ relaxation time for an atomic nucleus at a particular site;

"$T_2$" is a $T_2$ relaxation time for an atomic nucleus at a particular site; and "dv/dT" is a temperature coefficient for a particular NQR frequency.

TABLE 2

| Chemical Species | Sites | | | | Spectral Lines At Each Site | | | | |
|---|---|---|---|---|---|---|---|---|---|
| | Site # | Type | Weight % | QCC | η | NQR Frequency (kHz) | FWHM (kHz) | $T_1$ (ms) | $T_2$ (ms) | dv/dT (kHz/° C.) |
| Glycine ($C_2H_5NO_2$) | 1 | amine-$^{14}$N | 18.7 | 1193 | 0.528 | 1052 | 2.8 | 43.4 | 12.5 | -.0195 |
| | | | | | | 737 | 0.8 | 50.0 | 17.1 | -.205 |
| Sodium Nitrite ($NaNO_2$) | 1 | nitro-$^{14}$N | 20.2 | 5497 | 0.378 | 4642 | 0.16 | 90.3 | 5.3 | -1.6 |
| | | | | | | 3604 | 0.12 | 280 | 3.3 | -1.2 |
| | | | | | | 1038 | 0.10 | 328 | 5.1 | -0.4 |
| Potassium Nitrate ($KNO_3$) | 1 | nitro-$^{14}$N | 13.9 | 751 | 0.022 | 567 | 0.11 | 20.1 (s) | — | -0.23 |
| | | | | | | 559 | 0.11 | 24.5 (s) | — | -0.19 |
| | 2 | $^{39}$K | 36.0 | 1326 | 0.171 | 665 | 0.80 | 1.9 (s) | — | -0.58 |
| Ammonium Nitrate ($H_4N_2O_3$) | 1 | nitro-$^{14}$N | 17.5 | 613 | 0.241 | 497 | 0.05 | 14 (s) | — | -0.46 |
| | | | | | | 423 | 0.06 | 16.6 (s) | — | 0.12 |
| L-proline ($C_5H_9NO_2$) | 1 | amine-$^{14}$N | 12.2 | 1495 | 0.975 | 1486 | 0.50 | 1.2 (s) | — | -0.546 |
| | | | | | | 757 | 0.12 | 2.4 (s) | — | -0.315 |
| | | | | | | 729 | 0.37 | 1.4 (s) | — | -0.211 |

TABLE 2-continued

| | | | | | Spectral Lines At Each Site | | | | |
|---|---|---|---|---|---|---|---|---|---|
| Chemical | Sites | | | | NQR Frequency | FWHM | $T_1$ | $T_2$ | dv/dT |
| Species | Site # | Type | Weight % | QCC | η | (kHz) | (kHz) | (ms) | (ms) | (kHz/° C.) |
| RDX ($C_3H_6N_6O_6$) | 1 | amine-$^{14}$N | 6.3 | 5715 | 0.622 | 5192 | 0.2 | 12.6 | 8.2 | −0.43 |
| | | | | | | 3410 | 0.4 | 11.1 | 6.2 | −0.06 |
| | | | | | | 1782 | — | — | — | −0.37 |
| | 2 | amine-$^{14}$N | 6.3 | 5799 | 0.615 | 5240 | 0.43 | 12.3 | 7.1 | −0.47 |
| | | | | | | 3458 | 0.54 | 12.1 | 5.7 | −0.33 |
| | | | | | | 1782 | — | — | — | −0.14 |
| | 3 | amine-$^{14}$N | 6.3 | 5604 | 0.602 | 5047 | 0.45 | 13.3 | 6.8 | −0.43 |
| | | | | | | 3159 | 0.43 | 14.6 | 6.3 | −0.27 |
| | | | | | | 1688 | — | — | — | −0.16 |
| | 4 | nitro-$^{14}$N | 6.3 | 394-460 | 1.0-0.41 | 405.1 | 0.25 | 15.9 | 7.3 | — |
| | | | | | | 396.2 | 0.3 | 18.1 | 6.2 | — |
| | | | | | | 381.4 | 0.3 | 13.5 | 7.5 | — |
| | 5 | nitro-$^{14}$N | 2 × 6.3 | 597 | 0.36 | 502.3 | 0.15 | 15.9 | 6.6 | −0.18 |
| | | | | | | 500.5 | 0.15 | 13.8 | 8.2 | −0.2 |
| | | | | | | 405.1 | 0.25 | 15.9 | 7.3 | — |
| | | | | | | 396.2 | 0.3 | 18.1 | 6.2 | — |
| | | | | | | 381.4 | 0.3 | 13.5 | 7.5 | — |
| | 6 | nitro-$^{14}$N | 2 × 6.3 | 597 | 0.36 | 502.3 | 0.15 | 15.9 | 6.6 | −0.18 |
| | | | | | | 500.5 | 0.15 | 13.8 | 8.2 | −0.2 |
| | | | | | | 405.1 | 0.25 | 15.9 | 7.3 | — |
| | | | | | | 396.2 | 0.3 | 18.1 | 6.2 | — |
| | | | | | | 381.4 | 0.3 | 13.5 | 7.5 | — |
| TNT ($C_7H_5N_3O_6$) | 1 | nitro-$^{14}$N | 3.1 | 1062 | 0.171 | 842 | 0.8 | 3.5 (s) | — | −0.181 |
| | | | | | | 751 | 0.7 | 2.2 (s) | — | −0.241 |
| | 2 | nitro-$^{14}$N | 3.1 | 1085 | 0.168 | 859 | 1.3 | 3 (s) | — | −0.223 |
| | | | | | | 768 | 0.7 | 9.8 (s) | — | −0.19 |
| | 3 | nitro-$^{14}$N | 3.1 | 1053 | 0.178 | 837 | 0.9 | 2.1 (s) | — | −0.122 |
| | | | | | | 743 | 0.4 | 3 (s) | — | −0.148 |
| | 4 | nitro-$^{14}$N | 3.1 | 1059 | 0.204 | 848 | 0.4 | 9.6 (s) | — | −0.151 |
| | | | | | | 740 | 1 | 5.5 (s) | — | −0.169 |
| | 5 | nitro-$^{14}$N | 3.1 | 1039 | 0.25 | 844 | 0.8 | 4.7 (s) | — | −0.121 |
| | | | | | | 714 | 0.7 | 4.3 (s) | — | −0.094 |
| | 6 | nitro-$^{14}$N | 3.1 | 1056 | 0.295 | 870 | 0.5 | 4 (s) | — | −0.109 |
| | | | | | | 714 | 0.7 | 4.3 (s) | — | −0.094 |
| Cocaine Hydrochloride ($C_{17}H_{21}NO_4 \cdot HCL$) | 1 | amine-$^{14}$N | 4.3 | 1178 | 0.263 | 961 | 4 | 2000 | 0.3 | −0.004 |
| | | | | | | 806 | 5 | 700 | 1.5 | −0.032 |
| | 2 | $^{35}$Cl | 7.7 | 3800-5060 | — | 2530 | 20 | 57 | 0.15 | — |
| Heroin Hydrochloride ($C_{21}H_{23}NO_5 \cdot HCl \cdot H20$) | 1 | amine-$^{14}$N | 3.3 | 1080-1440 (at 20° K) | — | 1080 (at 20° K) | — | — | — | — |

Illustrative embodiments described herein are not limited to detecting the chemical species described in Table 2. The chemical species presented in Table 2 are presented as non-limiting examples.

Figure 6:
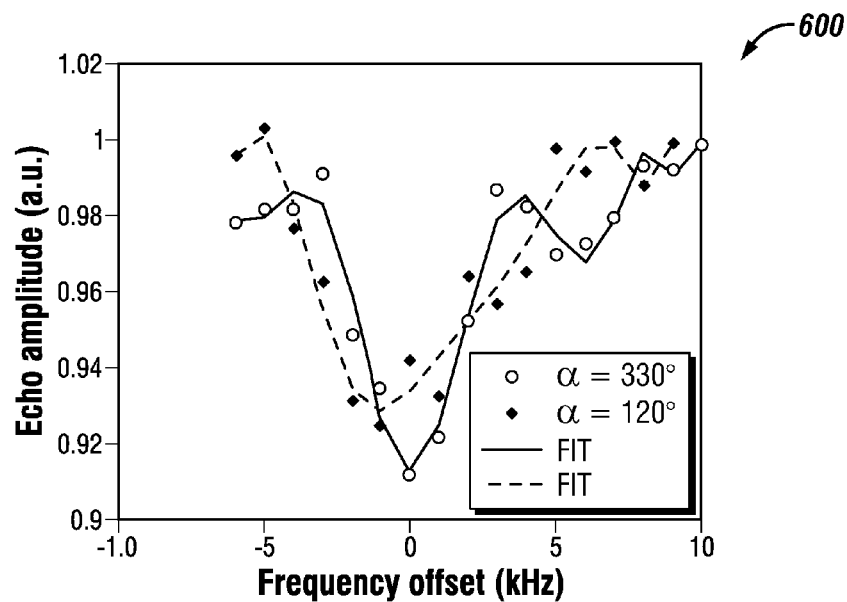
FIG. 6 shows a plot of echo amplitude versus frequency offset for a glycine sample in accordance with one embodiment of the present disclosure.

FIG. 6 shows a plot 600 of echo amplitude versus frequency offset for a glycine sample in accordance with one embodiment of the present disclosure. In particular, FIG. 6 shows the echo amplitudes, produced by a perturbation-detection sequence, as a function of the frequency of the perturbation pulse. FIG. 6 shows the results for nutation angles with α=340 degrees and α=120 degrees. The figure confirms that a resonant decrease in signal amplitude is present with a bandwidth of approximately ±2 kHz. This behavior indicates that the measurements reflect coupling between populations of the three-level NQR system. The sequence parameters for FIG. 6 include N=1024, $T_E$=1.5 ms, $N_E$=15, $T_p$=480 µs (β≈120 degrees), and $T_R$=200 ms. Echo amplitudes have been normalized to echo amplitudes produced by an SLSE sequence without a perturbation segment.

Figures 7, 8:
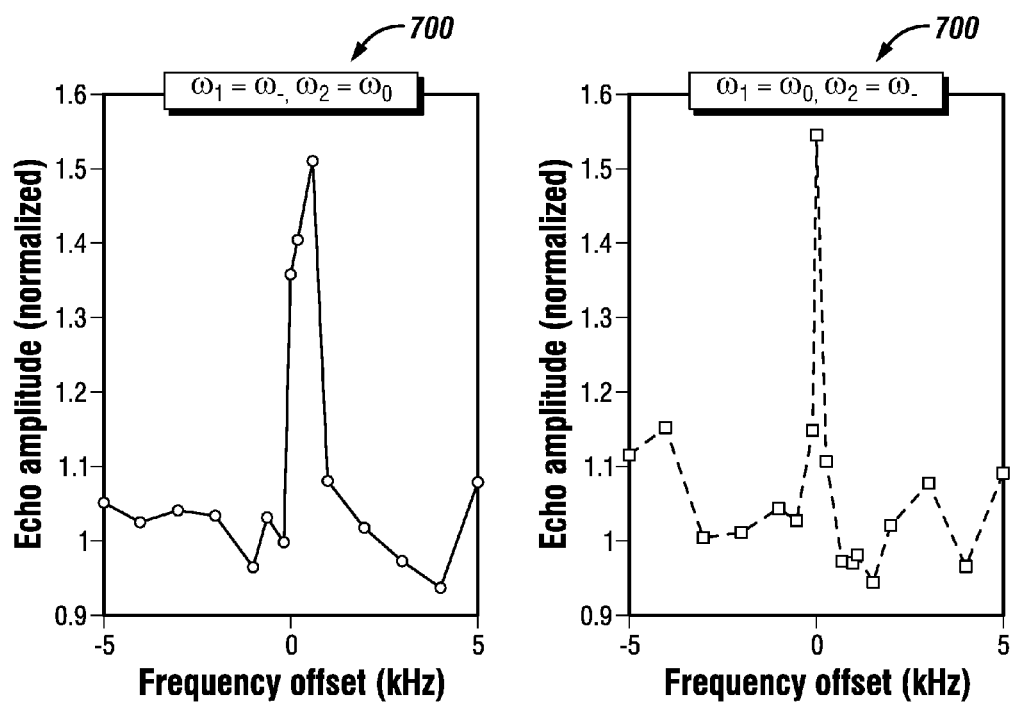
FIG. 7 shows a plot of normalized echo amplitude versus frequency offset for a L-proline sample in accordance with one embodiment of the present disclosure.
FIG. 8 shows another plot of normalized echo amplitude versus frequency offset for a L-proline sample in accordance with one embodiment of the present disclosure.

FIGS. 7 and 8 show plots 700, 800 of normalized echo amplitude versus frequency offset in accordance with one embodiment of the present disclosure. More specifically, FIGS. 7 and 8 show $^{14}$N NQR spectral lines for perturbation-detection pulse sequences applied to a sample of L-proline (e.g., $\omega_+/2\pi$=1486 kHz, $\omega_-/2\pi$=757 kHz, and $\omega_0/2\pi$=729 kHz at room temperature). For FIG. 7, the perturbation segment included one pulse applied at 757 kHz ($\omega_-/2\pi$) and the detection segment included an SLSE sequence applied at 729 kHz ($\omega_0/2\pi$) (e.g., Δω=0 at 757 kHz). For FIG. 8, the perturbation segment included one pulse applied at 729 kHz ($\omega_0/2\pi$) and the detection segment included an SLSE sequence applied at 757 kHz ($\omega_-/2\pi$) (e.g., Δω=0 at 729 kHz). In each case, at near resonant frequency (e.g., Δω=0), the signal amplitude increases by approximately 50%. This increase in signal amplitude conforms to the amplitude changes listed in Table 1. Sequence parameters for FIGS. 7 and 8 include N=128, $T_E$=1.5 ms and 1.7 ms respectively, $N_E$=50 and 60 respectively, $T_p$=480 µs (β≈115 degrees), and $T_R$=6 seconds. Echo amplitude has been normalized to echo amplitudes produced by an SLSE sequence without a perturbation segment.

Figure 9:
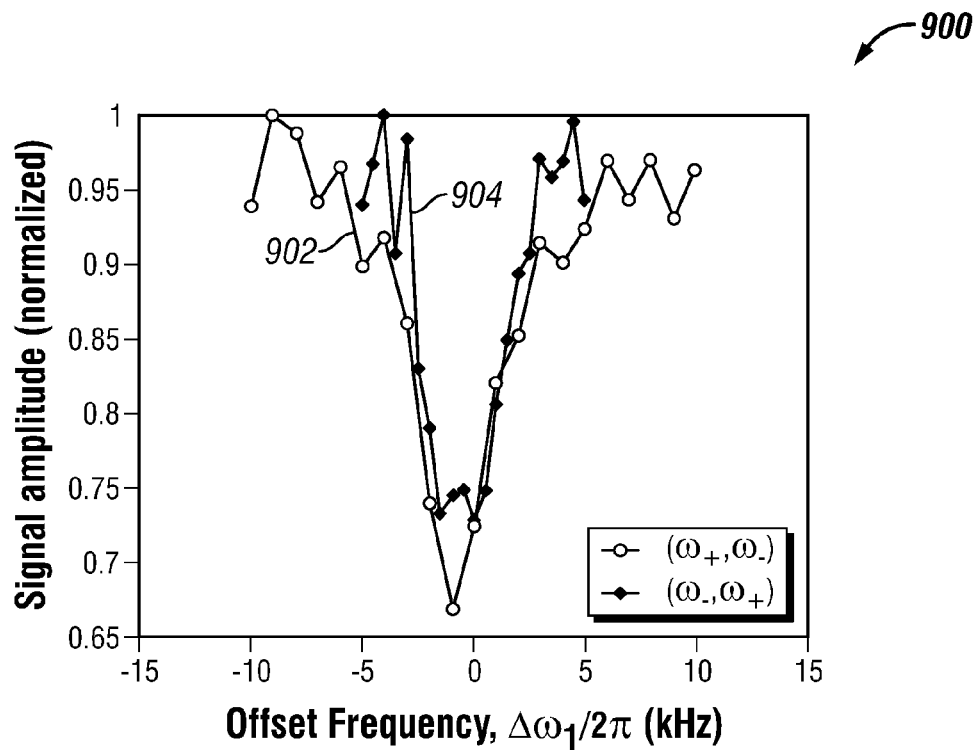
FIG. 9 shows a set of $^{14}$N NQR spectral lines for perturbation-detection pulse sequences applied to a sample of glycine in accordance with one embodiment of the present disclosure.

FIG. 9 shows a plot of normalized echo amplitude versus frequency offset in accordance with one embodiment of the present disclosure. More specifically, FIG. 9 shows $^{14}$N NQR spectral lines for perturbation-detection pulse sequences applied to a sample of glycine (e.g., $\omega_+/2\pi$=1052 kHz, $\omega_-/2\pi$=737 kHz, and $\omega_0/2\pi$=315 kHz). For the first line 902, the perturbation segment included one pulse applied at 1052 kHz ($\omega_+/2\pi$) and the detection segment included an SLSE sequence applied at 737 kHz ($\omega_-/2\pi$). For the second line 904, the perturbation segment included one pulse applied at 737 kHz ($\omega_-/2\pi$) and the detection segment included an SLSE sequence applied at 1052 kHz ($\omega_+/2\pi$). In both cases, the amplitude of the NQR signal decreases. These decreases in signal amplitude conform to the amplitude changes listed in Table 1. Sequence parameters for FIG. 9 include N=128, $T_E$=760 μs/800 μs, $N_E$=70, $T_p$=360 μs/260 μs for initial pulse and 120 μs/170 μs for later pulses, and $T_R$=0.4 seconds. Echo amplitude has been normalized to echo amplitudes produced by an SLSE sequence without a perturbation segment.

Figure 10:
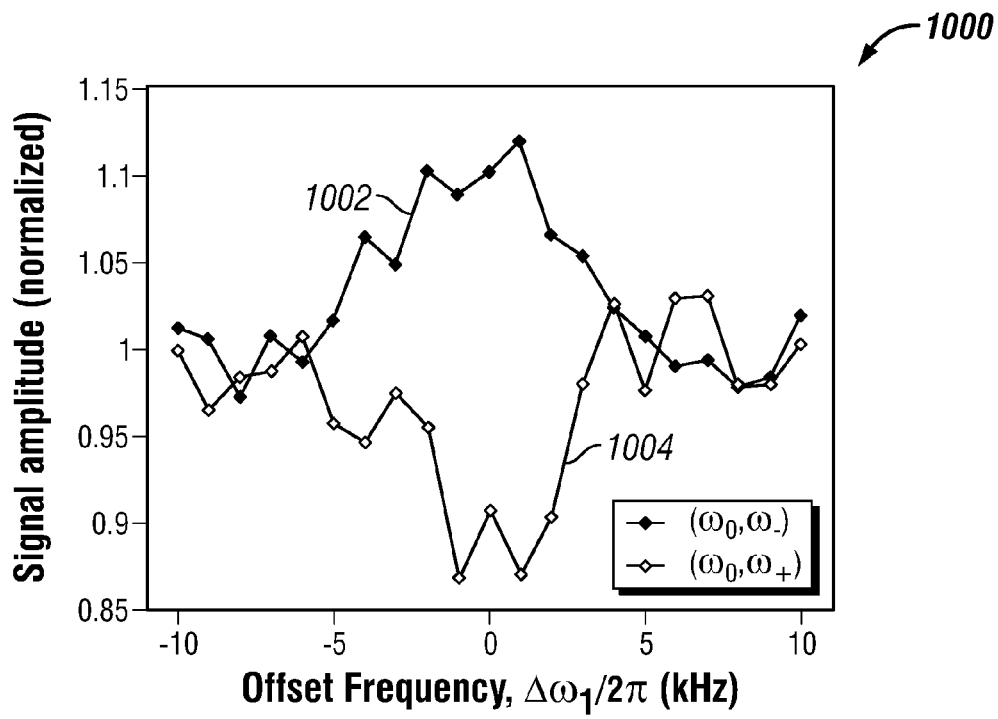
FIG. 10 shows another set of $^{14}$N NQR spectral lines for perturbation-detection pulse sequences applied to the sample of glycine in accordance with one embodiment of the present disclosure.

FIG. 10 show a plot of normalized echo amplitude versus frequency offset in accordance with another embodiment of the present disclosure. More specifically, FIG. 10 shows more $^{14}$N NQR spectral lines for perturbation-detection pulse sequences applied to the sample of glycine (e.g., $\omega_+/2\pi$=1052 kHz, $\omega_-/2\pi$=737 kHz, and $\omega_0/2\pi$=315 kHz). In this case, for the first line 1002, the perturbation segment included one pulse applied at 315 kHz ($\omega_0/2\pi$) and the detection segment included an SLSE sequence applied at 737 kHz ($\omega_-/2\pi$). For the second line 1004, the perturbation segment included one pulse applied at 315 kHz ($\omega_0/2\pi$) and the detection segment included an SLSE sequence applied at 1052 kHz ($\omega_+/2\pi$). In the first case 1002, the amplitude of the NQR signal increases, while in the second case 1004, the NQR signal decreases. These changes in signal amplitude again conform to the amplitude changes listed in Table 1. Sequence parameters for FIG. 10 include N=256, $T_E$=800 μs/850 μs, $N_E$=70/65, $T_p$=150 μs for initial pulse and 160 μs/225 μs for later pulses, and $T_R$=0.4 seconds. Echo amplitude has been normalized to echo amplitudes produced by an SLSE sequence without a perturbation segment.

Figure 11:
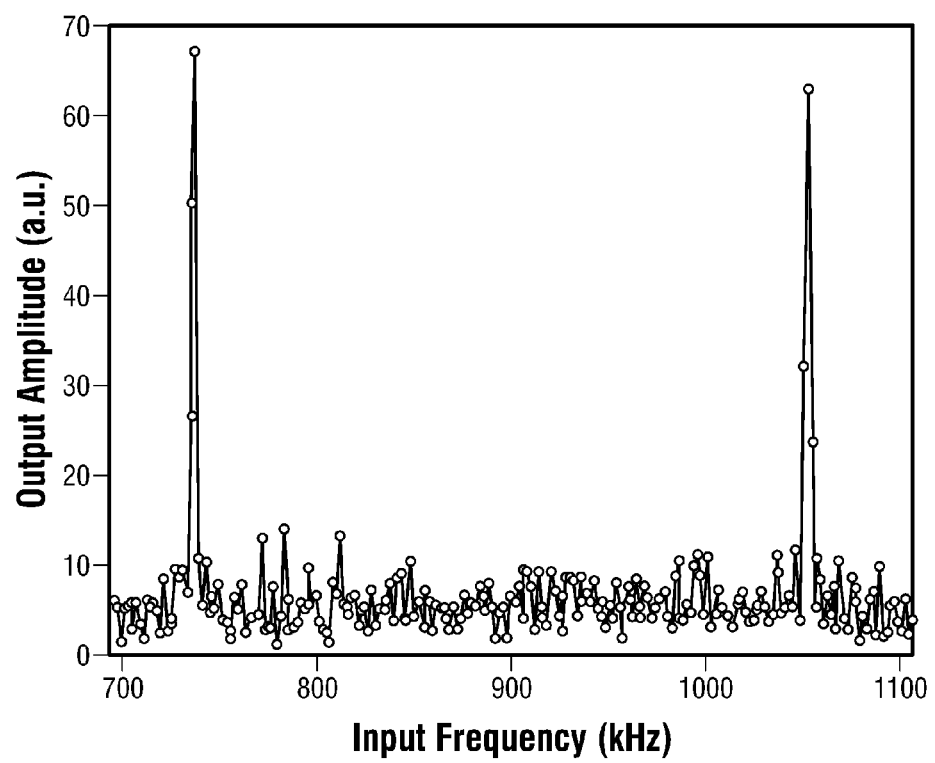
FIG. 11 shows a plot of signal amplitude versus pulse frequency for a sample containing glycine in accordance with one embodiment of the present disclosure.

FIG. 11 shows a broadband frequency sweep of a sample containing glycine. During this experiment, an SLSE sequence was applied at intervals of $\omega_{int}/2\pi$=10 kHz and the detected (e.g., measured) echoes were added together to improve signal to noise ratio (SNR). The spectrum of each echo was calculated using a fast Fourier transform (FFT) and then the spectrums were "stitched" together into a composite spectrum, as shown in the FIG. 11. The value of $\omega_{int}$ was chosen to be less than w (which varies between 2π×25.5 kHz and 2π×40.3 kHz), thus ensuring that the RF amplitude is approximately constant within each interval. This methodology provides for a final spectral resolution of $\Delta\omega/2\pi \approx 1/T_{acq}$=195 kHz by running a much coarser frequency sweep ($\omega_{int}/2\pi$=10 kHz), which reduces experimental time. Here $T_{acq}$=512 μs is the length of each echo acquisition window. Two NQR spectral lines are clearly visible at 737 kHz and 1.052 MHz. These correspond to the $\omega_+$ and $\omega_-$ transitions of glycine. Sequence parameters for FIG. 11 include $N_{avg}$=256, $T_p$ increases linearly from 52 μs (at 700 KHz) to 82 μs (at 1.1 MHz) to obtain a constant flip angle of 120 degrees, $T_E$=700 μs, $N_E$=80, and $T_R$=0.5 sec.

Further examples of two-dimensional NQR experiments are described herein. In these experiments, the frequency of the perturbation pulse is referred to as (18 in FIG. 1A) the perturbation frequency, and the frequency of the other pulses (20 in FIG. 1A) as the detection frequency. FIGS. 12A-12D show the results of a two-dimensional frequency scan of a glycine sample over the same frequency range as in FIG. 11. This result matches the theoretical plot shown in FIGS. 5A and 5B. The threshold plot clearly shows four negative peaks. The peaks are broader along the perturbation frequency axis, where their width is set by the bandwidth of the perturbation pulse, than along the detection frequency axis, where the width is set by the length of the echo acquisition windows. The two cross-peaks show that the lines at 737 kHz and 1.052 MHz have coupled populations, i.e., that they come from a single site. Moreover, the fact that both peaks are negative confirms that the lines correspond to the $\omega_-$ and $\omega_+$ transitions, respectively, as shown in Table 1.

Figure 12A:
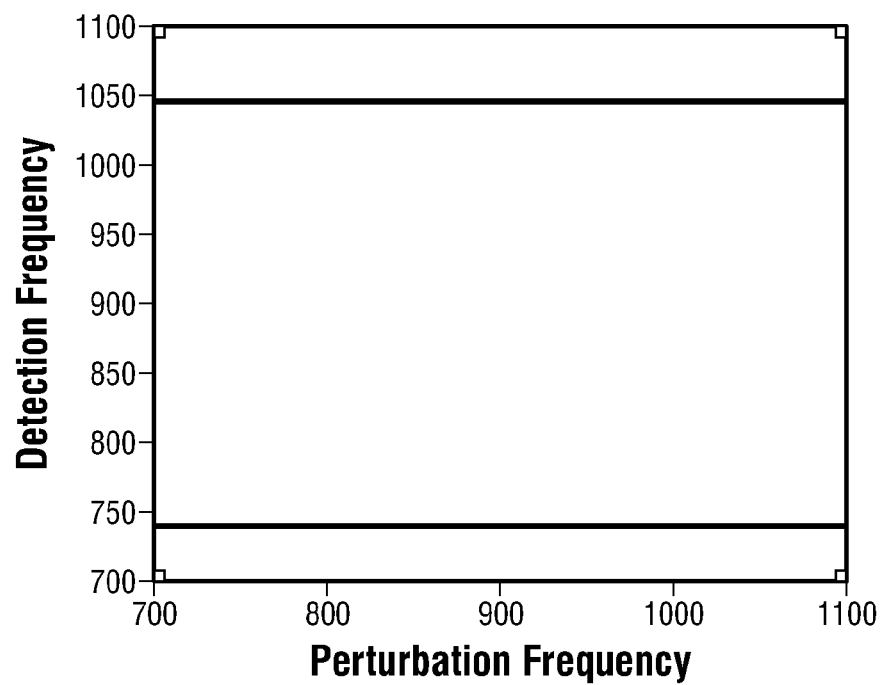
FIGS. 12A-12D show measured spectra for a glycine sample between 700 kHz and 1.1 MHz in accordance with one embodiment of the present disclosure.
Figure 12B:
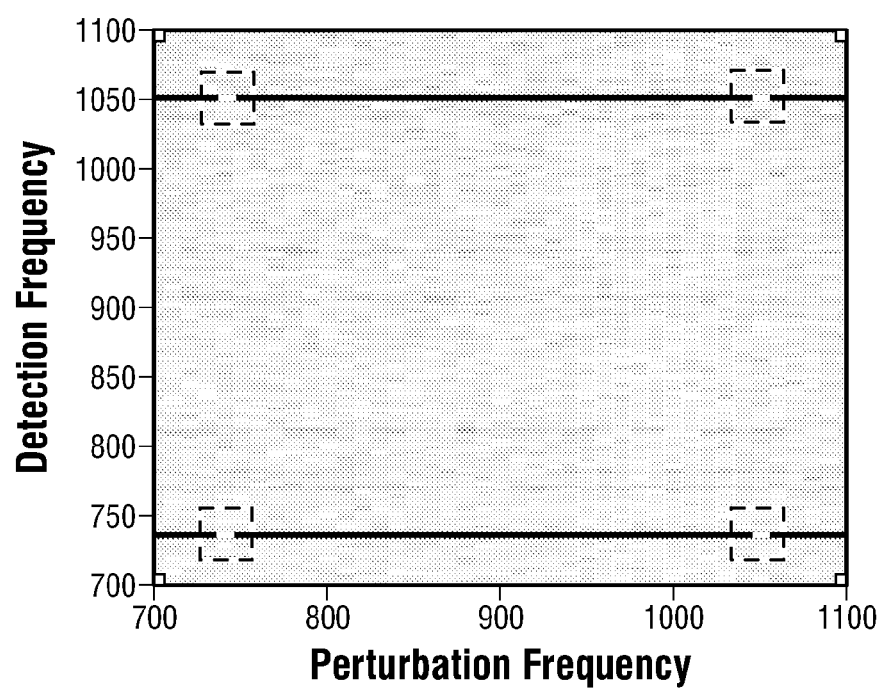
Figure 12C:
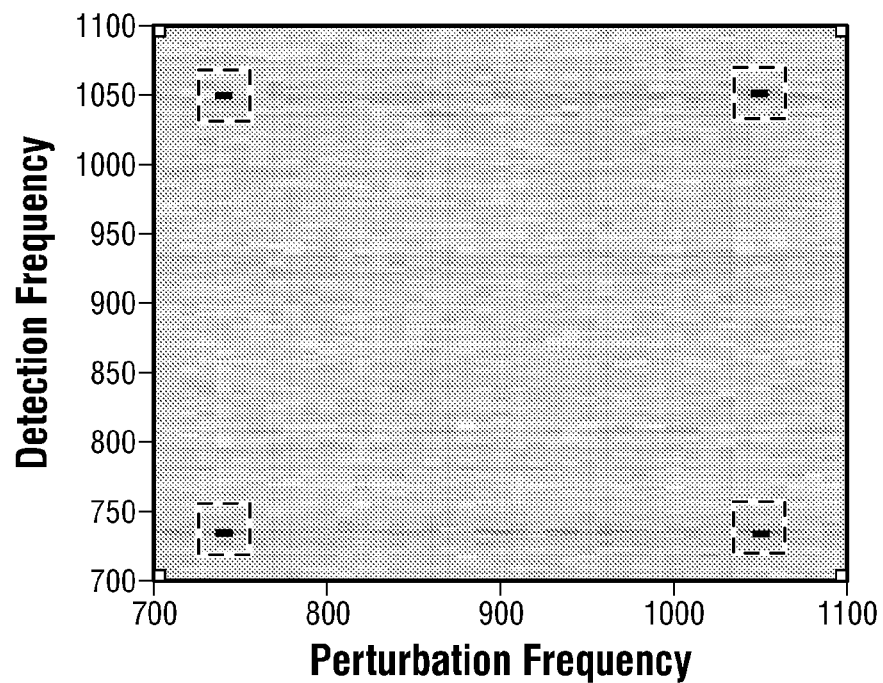
Figure 12D:
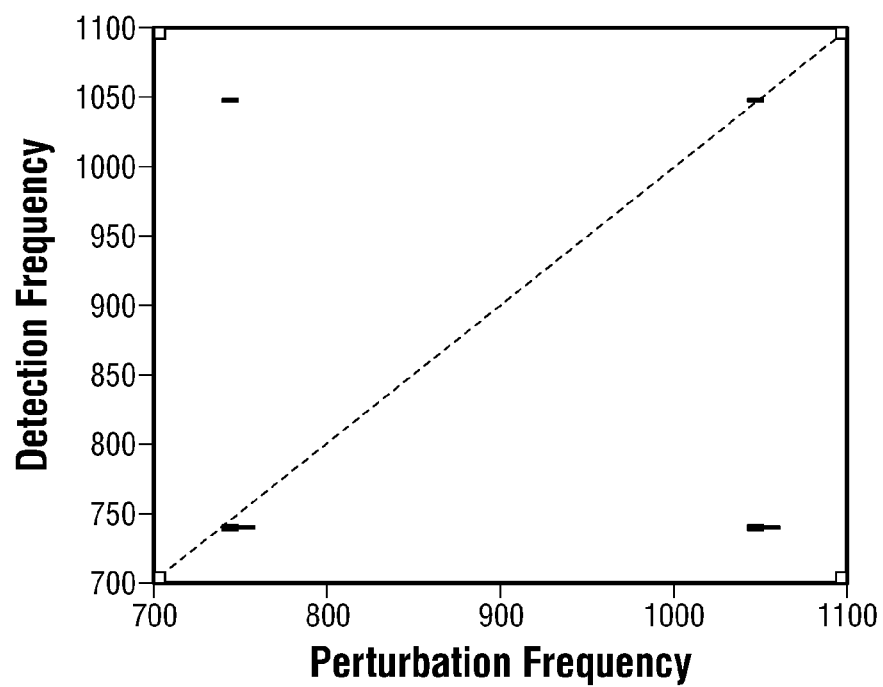

FIGS. 12A-12D show measured spectra of a glycine sample between 700 kHz and 1.1 MHz. The flip angle of the initial pulse was fixed at 257 degrees, while that of the detection pulses was fixed at 120 degrees. The interval size was $\omega_{int}/2\pi$=10 kHz along both axes. In addition, the "stitching" procedure used in FIG. 11 was used to improve the frequency resolution to $\Delta\omega/2\pi \approx 1/T_{acq}$=1.95 kHz along the detection frequency axis. In particular, FIG. 12A shows a reference spectrum with the initial (perturbation) pulse switched off. The $\omega_+$ and $\omega_-$ transitions of glycine are clearly visible. FIG. 12B shows a raw two-dimensional spectrum with the initial pulse switched on. The signal amplitude decreases noticeably in the four boxed regions. FIG. 12C shows a two-dimensional difference spectrum, obtained by subtracting the raw two-dimensional spectrum from the reference spectrum. FIG. 12D shows a two-dimensional difference spectrum, with the threshold level set to ±25% of the maximum value. The dashed line represents the diagonal ($\omega_1=\omega_2$).

Figure 13:
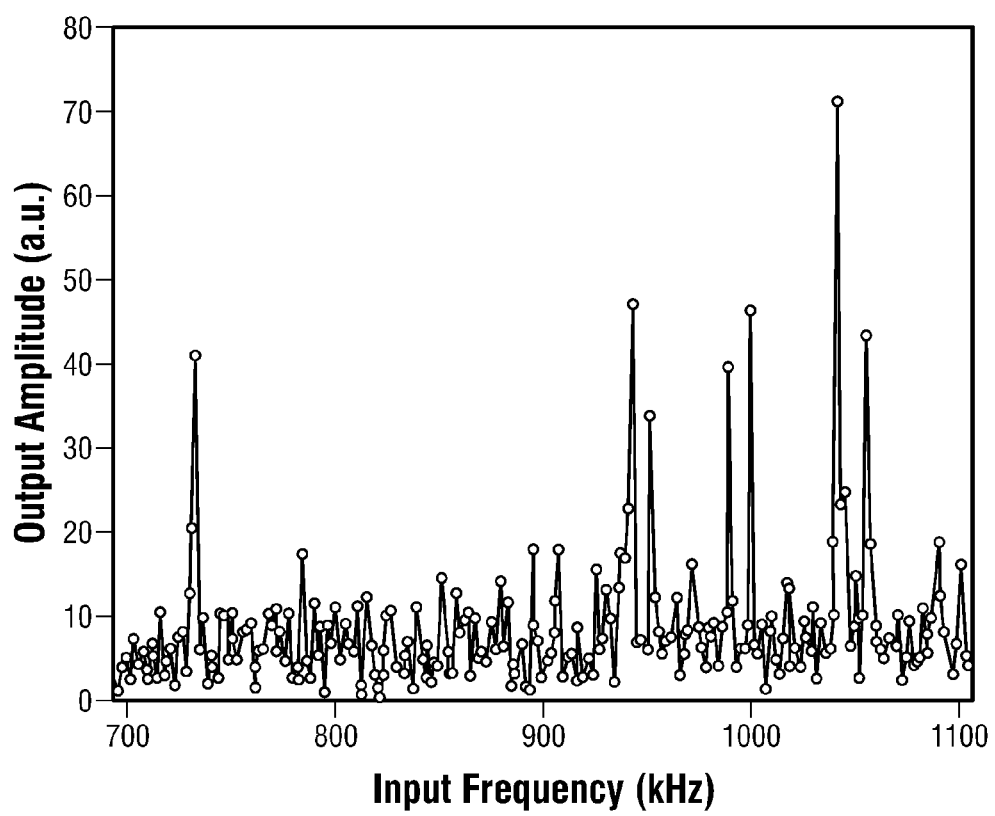
FIG. 13 shows a plot of signal amplitude versus pulse frequency for a sample containing glycine and sodium nitrite in accordance with one embodiment of the present disclosure.

FIG. 13 shows the results of a broadband frequency sweep performed on a mixture of glycine and sodium nitrate. Three NQR lines (at 737 kHz, 1.037 MHz, and 1.051 MHz) are labeled on the plot. The other lines visible in the spectrum arise from external interference, since they persist even when the RF pulses are switched off. The sample included a mixture of glycine (11.6 gm) and sodium nitrite (9.5 gm). Sequence parameters for FIG. 13 include $N_{avg}$=128, $T_p$ increases linearly from 52 μs (at 700 KHz) to 82 μs (at 1.1 MHz) to obtain a constant flip angle of 120 degrees, $T_E$=730 μs, $N_E$=130, $T_R$=1 sec.

Table 3 below shows the measured amplitude changes (in percent) for each line. The table clearly shows that line 2 is not coupled to lines 1 and 3. However, lines 1 and 3 are coupled to each other. Moreover, the fact that the amplitude changes related to lines 1 and 3 are negative confirms that these correspond to the $\omega_-$ and $\omega_+$ transitions of a single site (see Table 1). These results confirm that lines 1 and 3 are the $\omega_-$ and $\omega_+$ transitions of glycine, while line 2 is the $\omega_0$ transition of sodium nitrite.

TABLE 3

| | Perturbation frequency | | |
|---|---|---|---|
| Detection frequency | 1 | 2 | 3 |
| 1 | | −26.1 ± 7.8 | −48.6 ± 7.8 |
| 2 | −1.4 ± 2.9 | | −3.7 ± 2.9 |
| 3 | −26.0 ± 7.8 | −7.0 ± 7.8 | |

Table 3 was generated by applying perturbation-detection sequences at each pair of lines. In each case the flip angle of the perturbation pulse was fixed at 257 degrees, while that of the detection pulses was fixed at 120 degrees. The uncertainties correspond to one standard deviation.

It should also be noted that there is a statistically substantial decrease in amplitude (26.1%) when the signal detected at line 1 is perturbed by a pulse at line 2, even though lines 1 and 2 are not coupled to each other. This is because the frequencies of lines 2 and 3 are separated by only 15 kHz, which is comparable to the bandwidth of the initial pulse.

Figure 14:
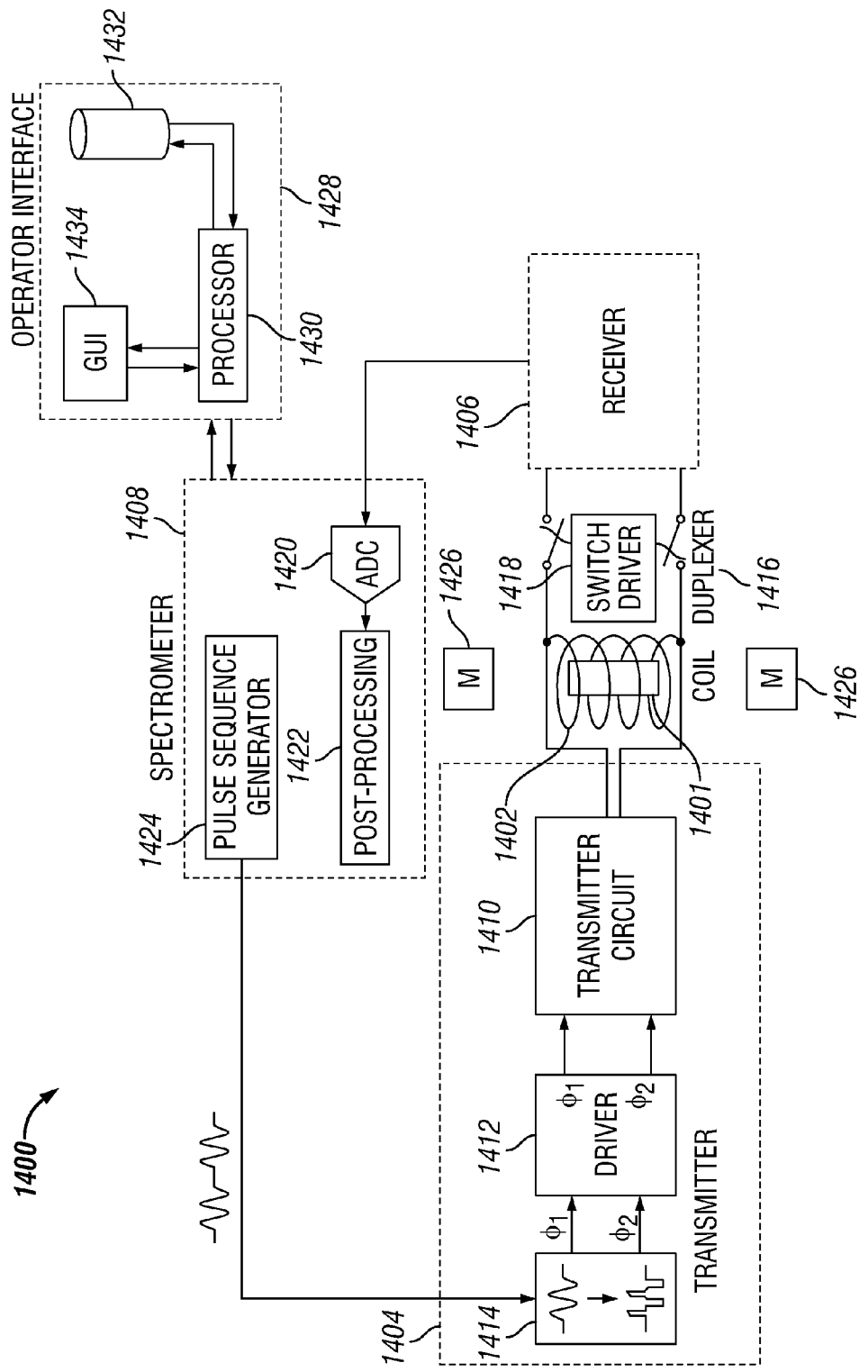
FIG. 14 shows a NQR system for applying NQR pulse sequences to a substance in accordance with one embodiment of the present disclosure.

FIG. 14 shows a NQR system 1400 for implementing the method described herein. The NQR system can be used as part of an explosive detection system, a drug detection system, or a wellbore logging system. The NQR system 1400 includes a coil 1402 that is coupled to NQR electronics 1404, 1406, 1408. A sample substance 1401 is located inside and/or outside of the coil 1402. The coil 1402 applies NQR pulse sequences to the substance 1401. The NQR electronics include a transmitter 1404 and a receiver 1406. Each of the transmitter 1404 and the receiver 1406 are coupled to the coil 1402. In some embodiments, however, the NQR system 1400 may include separate transmitter and receiver coils.

The NQR transmitter 1404 includes a NQR transmitter circuit 1410 that is coupled to the coil 1402. The transmitter circuit 1410 generates NQR pulse sequences and provides the NQR pulse sequences to the coil 1402. The NQR pulse sequences can be any of the NQR sequences described herein (e.g., multi-segment sequences, an interposed pulse sequences, SLSE sequences, and/or perturbation-detection sequences).

In some embodiments, the NMR transmitter 1404 uses a "tuned" NMR transmitter circuit 1410. A tuned NMR transmitter is tuned to a particular Larmor frequency using a capacitor that is coupled to the coil. The particular capacitance of the capacitor and the inductance of the coil determine the resonant frequency that is generated by the coil.

In other embodiments, a non-resonant transmitter circuit 1410 can be used to more effectively and efficiently apply the pulses described herein (e.g., the interposed sequences and the perturbation-detection sequences). A non-resonant transmitter circuit is "non-resonant" because the resonant frequency of the circuit does not need to match the Larmor frequency of interest. Although the non-resonant transmitter circuit and coil 1402 may use capacitors and have some associated capacitance, this capacitance is not specifically selected to match a Larmor frequency of interest. Instead, the transmitter circuit includes a plurality of switches that couple and decouple the coil 1402 with a power source. Operation of the switches generates a particular frequency. Thus, the frequency produced by the transmitter circuit can be modulated directly by a spectrometer. In some cases, the NQR transmitter 1404 (and the coil 1402) can switch between frequencies with a frequency difference as great as 10% of an initial applied frequency. In various other embodiments, the frequency can be even greater (e.g., 20% 30% or 50%). Also, in some embodiments, the NQR transmitter 1404 can switch between frequencies in less than 5 µs. In yet further embodiments, the NQR transmitter 1404 can switch between frequencies in less than 20 µs or 50 µs. Furthermore, in some embodiments, the NQR transmitter 1404 can operate within a frequency range of 50 kHz to 10 MHz.

Further details regarding non-resonant transmitters are provided in U.S. Publication No. 2012/0001629 published on Jan. 5, 2012; U.S. application Ser. No. 13/774,457, filed on Feb. 22, 2013, and U.S. patent application Ser. No. 13/963,826, filed on Aug. 9, 2013. These references are incorporated by reference in their entireties.

As shown in FIG. 14, the coil 1402 is also coupled to a NQR receiver 1406 so that NQR resonant signals that are generated within the substance 1401 can be processed (e.g., detected, amplified and analyzed). In one specific embodiment, the NQR receiver 1406 is a broadband NQR receiver, which can receive and process resonant NQR signals over a frequency range of interest suitable for NQR applications. The coil 1402 is coupled to the NQR receiver 1406 using a duplexer 1416. The duplexer 1416 decouples the NQR receiver 1406 from the coil 1402 when the coil is operating in a transmitting mode (e.g., transmitting an NQR pulse sequence). In one particular embodiment, the duplexer 1416 includes switches and a switch driver 1418 that opens the switches during a transmitting mode and closes the switches during a receiving mode of operation. In this manner, the duplexer 1416 protects the receiver 1406 during a transmitting mode. A duplexer may not be used when the NQR system 1400 includes separate transmit and receive coils.

The NQR system also includes a spectrometer 1408 that is used to provide NQR pulse sequences to the NQR transmitter 1404 and to analyze the NQR signal received from the NQR receiver 1406. In various embodiments, the detected NQR signal is output by the NQR receiver 1406 in analog form. In such embodiments, the spectrometer 1408 may include a digitizer 1420 (e.g., analog-to-digital converter) for converting the detected NQR signal into digital data. Furthermore, in various embodiments, demodulation of the NQR signal can occur within the spectrometer 1408. In various other embodiments, however, demodulation of the NQR signal can also occur within the NQR receiver 1406. The spectrometer 1416 also includes a post-processor 1422 that is used to interpret the detected digital NQR data and to determine NQR properties from the detected data. This data can be presented to a user using an operator interface with a graphical user interface (GUI). The spectrometer 1408 also includes a pulse sequence generator 1424 that generates NQR pulse sequences based upon parameters selected by an operator at the operator interface. The pulse sequence generator provides the sequences to the NQR transmitter 1404. In one particular embodiment, the spectrometer 1408 is a KEA™, which can be obtained from Magritek of Wellington, New Zealand. The spectrometer 1408 can be controlled from the operator interface using PROSPA™ software, which can also be obtained from Magritek.

Further details of NQR electronics, NQR transmitters, non-resonant transmitter circuits, and NQR receivers are described in U.S. Publication No. 2012/0001629 published on Jan. 5, 2012, and PCT Publication No. WO 2013/134474, published on Sep. 12, 2013. Both of these references are incorporated herein, in their entireties, by reference.

As shown in FIG. 14, the NQR system 1400 may also include a device 1426 for applying a static magnetic field to the substance 1401. In some embodiments, the device 1426 is a magnet or an array of magnets. The magnets can be formed from a samarium-cobalt (SmCo) magnetic material. In other embodiments, no electro-magnetic device 1426 is provided for applying a static magnetic field. The NQR methods and pulses described herein can be performed without a static magnetic field. However, in some embodiments, a small magnetic field can be used. In particular, the presence of the earth's magnetic field is not detrimental to the experiments.

The NQR system 1400 also includes an operator interface 1428 for communicating with the spectrometer 1408. The operator interface 1428 includes a computer system. The computer system may include a computer processor 1430 (e.g., a microprocessor, microcontroller, digital signal processor, or general purpose computer) for executing any of the methods and processes described herein. The computer system may further include a memory 1432 such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCM-CIA card), or other memory device. The memory 1432 can be used to store computer instructions (e.g., computer program code) that are interpreted and executed by the processor 1430.

NQR pulse sequences may be implemented as a series of computer instructions (e.g., software or firmware) fixed on a non-transitory tangible medium, such as a computer readable medium (e.g., a memory), or transmittable to the computer system, via a modem or other interface device, such as a communications adapter connected to a network over a tangible medium (e.g., optical or analog communications lines). The series of computer instructions can embody all or part of the NQR pulse sequences described herein. The processor 1430 may be configured to retrieve the sequences from the memory 1432 and provide instructions to the NQR electronics 1404, 1406, 1408 to apply the sequences to the substance 1401. The detected resonant signals may also be communicated from the NQR electronics 1404, 1406, 1408 to the processor 1430 for storage on the memory 1432.

The NQR system 1400 may also include a temperature sensor (not shown) within or adjacent to the sample 1401 and coupled to the operator interface 1428 so that the NQR system 1400 can correctly determine resonant frequencies of atomic nuclei in an environment with dynamic temperatures. Many NQR transition frequencies are affected by temperature.

The operator interface 1428 also supports the graphical user interface 1434 (GUI) (e.g., a monitor, a touch screen, a mouse, a keyboard and/or a joystick). The GUI 1434 allows an operator to control and communicate with the NQR electronics 1404, 1406, 1408. In various embodiments, the operator interface 1428 can be used to perform functions selected from the following non-limiting list:

Communicate instructions to the NQR electronics 1404, 1406, 1408 to initiate and/or terminate NQR measurements;

Communicate instructions to change parameters of NQR sequences to the NQR electronics (e.g., pulse amplitude of sequences, pulse lengths, timing between pulses, shape of pulses, and/or frequency of pulses);

Communicate detected NQR signal data from the NQR electronics 1404, 1406, 1408 to the operator interface 1428;

Communicate NQR pulse sequences from the operator interface 1428 to the NQR electronics 1404, 1406, 1408;

Perform analysis at the operator interface 1428 of detected NQR signal data to determine NQR properties of substances;

Display various plots of NQR properties to the operator at the operator interface 1428; and Communicate NQR pulse sequences from the operator interface 1428 to the NQR electronics 1404, 1406, 1408.

In various embodiments, the NQR electronics 1404, 1406, 1408 and the operator interface 1428 are physically located in the same place as a single system. This may be the case when the system is used in a surface environment, such as a building or laboratory (e.g., a bomb detection system or a drug detection system).

Illustrative embodiments of the present disclosure are not limited to the NQR system 1400 shown in FIG. 14. Various modifications can be made to the system. For example, in one specific embodiment, the NQR electronics 1404, 1406, 1408 include an additional computer system that supports the NQR electronics. In such an embodiment, the NQR electronics 1404, 1406, 1408 and operator interface 1428 may include their own communication modules, which provide for communication between the NQR electronics and the operator interface. A communications link between the communication modules can be established using, for example, a hard-wired link, an optical link, acoustic link, and/or a wireless link. By using the communication modules, the NQR electronics 1404, 1406, 1408 and the operator interface 1428 can be physically located in two separate locations. For example, in a wellbore application, the NQR electronics 1404, 1406, 1408 can be located downhole, while the operator interface 1428 is located at the surface.

Furthermore, in various embodiments, the NQR system 1400 can operate between an NQR mode and a NMR mode. In other words, the NQR system can apply both NQR pulse sequences and NMR pulse sequences to a substance of interest.

Various embodiments of the present disclosure have application in non-invasive detection of chemical species. In various embodiments, the NQR system, NQR methods (e.g., generating difference spectrums), and NQR sequences (e.g., interposed sequences, SLSE sequences, reference sequences, and/or perturbation-detection sequences) described herein can be used for detection of explosives, such as ammonium nitrate, TNT, and/or RDX. In one example, the NQR system is used to detect explosives concealed in luggage at airports or border crossings. In another example, the NQR system is used to detect landmines in a battlefield environment. In further embodiments, the NQR system and NQR sequences described herein can be used for detection of illegal drug detection, such as heroin hydro-chloride and/or cocaine hydro-chloride. Various embodiments described herein can also be used for detecting counterfeit or adulterated versions of legal drugs, such as metformin and paracetamol.

Illustrative embodiments of the present disclosure are also directed to oil and gas field applications. For example, in one specific example, the NQR system and NQR sequences described herein can be used to detect and determine the composition of kerogen. Kerogen contains nitrogen which can be detected according to the illustrative embodiments described herein. Kerogen is a solid mixture of organic chemical compounds that make up a portion of the organic matter in sedimentary rocks. Oil shale, an organic-rich fine-grained sedimentary rock, contains significant amounts of kerogen, from which liquid hydrocarbons called shale oil can be produced. Kerogen is a mixture of organic materials, rather than a specific chemical, and therefore does not have a unique chemical formula. The chemical composition of kerogen can vary distinctively from sample to sample. As an example, kerogen from the Green River Formation oil shale deposit of western North America contains elements in the following proportions: carbon 215:hydrogen 330:oxygen 12:nitrogen 5:sulfur 1. Thus, the fraction of nitrogen by weight is 5/563=0.89% in this case. However, analysis of a variety of other kerogen samples shows that this fraction can vary between 0.8% and 2%. Oil shale contains a lower percentage of organic matter than coal. In commercial grades of oil shale, the ratio of organic matter to mineral matter lies approximately between 0.75:5 and 1.5:5 (13% and 23%). Thus, the fraction of nitrogen in oil shale ranges from 0.12% to 0.46% (approximately 1 in 800 to 1 in 200). The resultant NQR resonant frequencies for shales can be determined by identifying where so-called "quadrupole dips" occur in measurements of biological samples using field cycling NMR spectrometers. A quadrupole dip is a reduction in proton $T_1$ relaxation time (e.g., 10%-15% reduction) due to cross-relaxation between protons and adjacent nitrogen atoms in proteins and amino acids. These dips can be centered at 650 kHz, 2.1 MHz, and 2.75 MHz. An NQR oil and gas field tool is described below.

Figure 15:
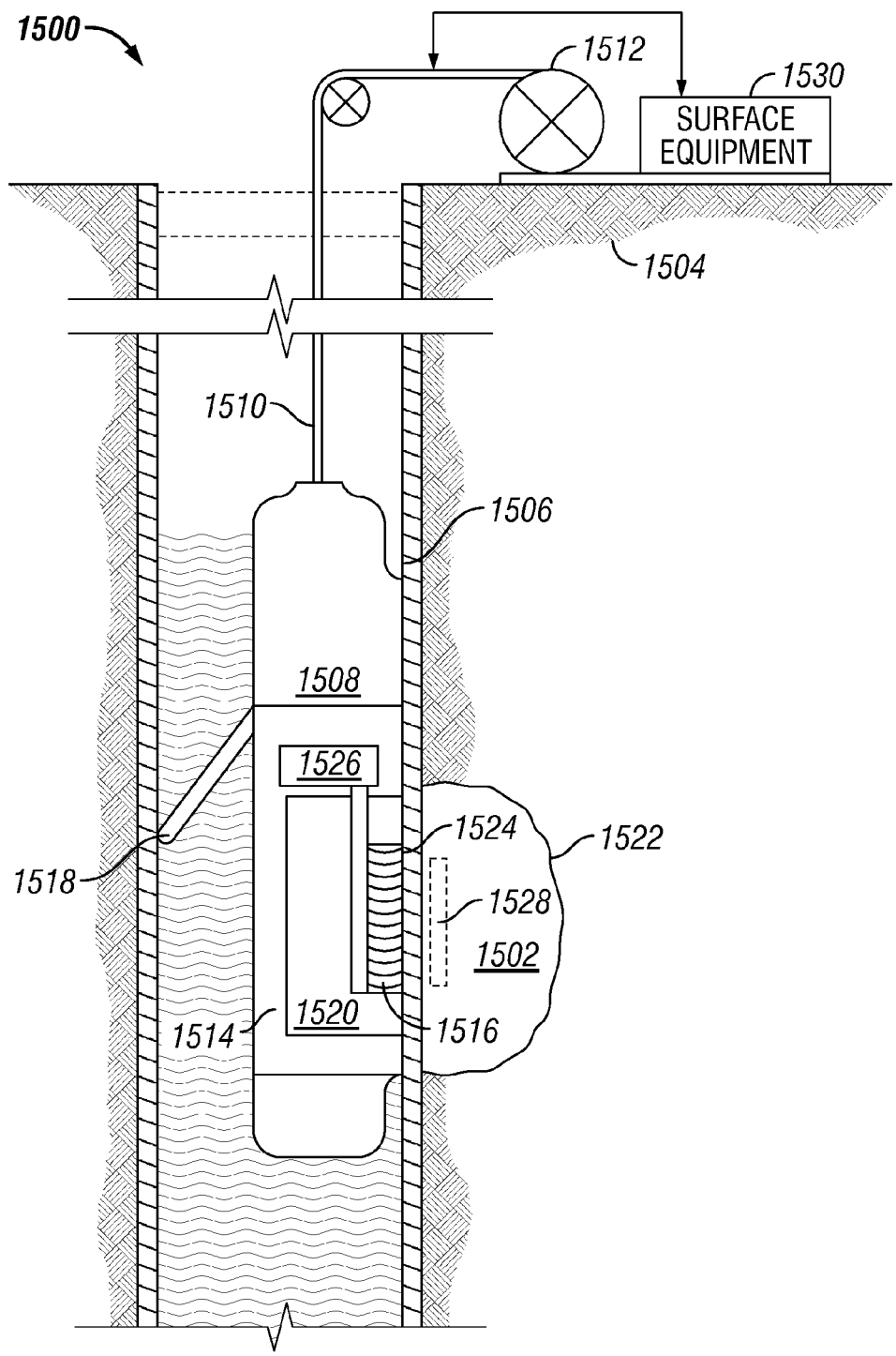
FIG. 15 shows a wellbore logging tool in accordance with one embodiment of the present disclosure.

FIG. 15 shows a wellbore logging tool 1500 for applying NQR sequences to a substance 1502 in accordance with one embodiment of the present disclosure. In this case, the wellbore logging tool is a wireline system 1500 that is used to investigate, in situ, a substance 1502 within an earth formation 1504 surrounding a wellbore 1506 to determine a characteristic of the substance (e.g., characteristics of solids and liquids within the earth formation). As shown in FIG. 15, a wireline tool 1508 is disposed within the wellbore 1506 and suspended on an armored cable 1510. A length of the cable 1510 determines the depth of the wireline tool 1508 within the wellbore 1506. The length of cable is controlled by a mechanism at the surface, such as a drum and winch system 1512. Although the wireline tool 1508 is shown as a single body in FIG. 15, the tool may alternatively include separate bodies.

As shown in FIG. 15, the wireline tool 1508 includes an NQR logging module 1514 that can used to apply any of the NQR sequences described herein (e.g., a multi-segment sequence, an interposed segment sequence, SLSE sequence, and/or perturbation-detection sequence). The NQR logging module 1514 includes a face 1516 that is shaped to contact the wellbore wall 1506 with minimal gaps or standoff. In some embodiments, a retractable arm 1518 is used to press the body of the wireline tool 1508 and the face 1516 against the wellbore wall 1506. In some embodiments, the NQR logging module 1514 also includes an electro-magnetic device 1520 for applying a static magnetic field to a sensitivity zone 1522 within the earth formation 1504. As explained above, in some embodiments, the electro-magnetic device 1520 is a magnet or an array of magnets formed from a magnetic material. In other embodiments, the logging module 1514 lacks the electro-magnetic device 1520.

The NQR logging module 1514 also includes at least one coil 1524 and NQR electronics 1526 electronically coupled to the coil. The coil 1516 and NQR electronics 1526 apply an oscillating field to an area of interest 1528 within the earth formation 1504. The area of interest 1502 may be located within the sensitivity zone 1522 of the electromagnetic device 1520 (if the device is used). In accordance with exemplary embodiments of the present disclosure, the oscillating field applied to the earth formation 1504 includes any of the NQR sequences described herein (e.g., interposed sequences, SLSE sequences, reference sequences, and/or perturbation-detection sequences). The oscillating field generates NQR signals within the area of interest 1528. These NQR signals are detected by the coil 1524. The detected NQR signals are used to determine characteristics of the substance 1502 within the area of interest 1528.

The wireline system 1500 includes surface equipment 1530 for supporting the wireline tool 1508 within the wellbore 1506. In various embodiments, the surface equipment 1530 includes a power supply for providing electrical power to the wireline tool 1508. The surface equipment 1530 also includes an operator interface for communicating with the NQR logging module 1514. Such an operator interface has already been described with reference to FIG. 14. In some embodiments, the NQR logging module 1514 and operator interface communicate through the armored cable 1510.

The method and systems described herein are not limited to any particular wellbore application. The NQR systems and methods described herein can be used with wireline systems, such as the one shown in FIGS. 15. Also, the methods and systems described herein can be applied to logging-while-drilling (LWD) systems (e.g., a LWD tools) or measuring-while-drilling systems (e.g., MWD tools). Illustrative embodiments can also be used with any suitable means of conveyance, such as armored cable, drill pipe, or coiled tubing.

Although several example embodiments have been described in detail above, those skilled in the art will readily appreciate that many modifications are possible in the example embodiments without materially departing from the scope of this disclosure. Accordingly, such modifications are intended to be included within the scope of this disclosure.

We claim:

1. A method for identifying chemical species within a substance using nuclear quadrupole resonance (NQR), the method comprising:
   applying a plurality of NQR perturbation-detection pulse sequences to the substance, wherein each perturbation-detection pulse sequence includes:
      a perturbation segment at a perturbation frequency; and
      a detection segment at a second frequency, wherein at least one of the perturbation frequency and the second frequency are varied for each pulse sequence and the perturbation frequency and second frequency are different frequencies;
   detecting a perturbation-detection set of NQR signals generated within the substance by each of the perturbation-detection pulse sequences;
   applying a plurality of NQR reference pulse sequences to the substance, wherein each reference pulse sequence is applied at a reference frequency and the reference frequency is varied for each pulse sequence;
   detecting a reference set of NQR signals generated within the substance by each of the reference pulse sequences; and
   identifying a chemical species within the substance by comparing the perturbation-detection set of NQR signals and the reference set of NQR signals.

2. The method of claim 1, wherein identifying the chemical species within the substance comprises:
   using the set of perturbation-detection NQR signals to generate a two-dimensional spectrum of the perturbation frequency and the second frequency;
   using the reference set of NQR signals to generate a reference spectrum for the reference frequency; and
   comparing the two-dimensional spectrum to the reference spectrum to identify the chemical species within the substance.

3. The method of claim 2, wherein the comparing the two-dimensional spectrum to the reference spectrum comprises:
   generating a difference spectrum using the two-dimensional spectrum and the reference spectrum; and
   identifying peaks within the difference spectrum.

4. The method of claim 2, wherein the second frequency is varied over a set of different frequencies and the reference frequency is varied over the same set of different frequencies.

5. The method of claim 2, wherein the second frequency is varied a plurality of times for each perturbation frequency.

6. The method of claim 2, wherein the plurality of reference pulse sequences are applied to the substance before the plurality of perturbation-detection pulse sequences are applied to the substance.

7. The method of claim 6, further comprising:
identifying a plurality of peaks within the reference spectrum generated by the reference set of NQR signals; and
selecting the perturbation frequency and the second frequency in the plurality of NQR perturbation-detection pulse sequences using frequencies associated with the identified peaks in the reference spectrum.

8. The method of claim 7, wherein the chemical species is selected from the group consisting of: Glycine, Proline, Ammonium Nitrate, TNT, RDX, Cocaine Hydrochloride, and Heroin Hydrochloride.

9. The method of claim 1, wherein the chemical species is a chemical compound that includes atomic nuclei selected from the group consisting of: nitrogen, chlorine, potassium, and copper.

10. The method of claim 1, wherein at least one NQR perturbation-detection pulse sequence of the plurality of perturbation-detection pulse sequences is at least partially interposed within another perturbation-detection pulse sequence.

11. The method of claim 1, wherein each NQR pulse sequence is applied to the substance using a coil and a NQR transmitter comprising a non-resonant NQR transmitter circuit electronically coupled to the coil.

12. A system comprising:
at least one coil for applying a nuclear quadrupole resonance (NQR) pulse sequences to a substance and for detecting NQR signals generated within the substance;
a NQR transmitter electronically coupled to the at least one coil and configured to generate and transmit NQR pulses sequences to the coil;
a NQR receiver coupled to the at least one coil and configured to process detected NQR signals;
a processor; and
a memory storing instructions executable by the processor to perform processes that include:
providing a plurality of NQR perturbation-detection pulse sequences to the NQR transmitter, wherein each perturbation-detection pulse sequence includes:
a perturbation segment at a perturbation frequency; and
a detection segment at a second frequency, wherein at least one of the perturbation frequency and the second frequency are varied for each pulse sequence and the perturbation frequency and second frequencies are different frequencies;
providing a plurality of NQR reference pulse sequences to the NQR transmitter, wherein each reference pulse sequence is applied at a reference frequency and the reference frequency is varied for each pulse sequence;
receiving from the NQR transmitter (i) a perturbation-detection set of NQR signals generated within the substance by each of the perturbation-detection pulse sequences and (ii) a reference set of NQR signals generated within the substance by each of the reference pulse sequences; and
identifying a chemical species within the substance by comparing the perturbation-detection set of NQR signals and the reference set of NQR signals.

13. The system of claim 12, wherein the NQR transmitter comprises a non-resonant NQR transmitter circuit.

14. The system of claim 12, wherein the system comprises an explosive detection system.

15. The system of claim 12, wherein the system comprises a drug detection system.

16. The system of claim 12, wherein the system comprises a wellbore logging system.

17. The system of claim 12, wherein the memory stores instructions executable by the processor to perform processes that further include:
using the set of perturbation-detection NQR signals to generate a two-dimensional spectrum of the perturbation frequency versus the second frequency;
using the reference set of NQR signals to generate a reference spectrum for the reference frequency; and
comparing the two-dimensional spectrum to the reference spectrum to identify the chemical species within the substance.

18. The system of claim 17, wherein the memory stores instructions executable by the processor to perform processes that further include:
generating a difference spectrum using the two-dimensional spectrum and the reference spectrum; and
identifying peaks within the difference spectrum.

19. The system of claim 17, wherein the memory stores instructions executable by the processor to perform processes that further include:
identifying a plurality of peaks within the reference spectrum generated by the reference set of NQR signals; and
selecting the perturbation frequency and second frequency in the plurality of NQR perturbation-detection pulse sequences using frequencies associated with the identified peaks in the reference spectrum.

20. The system of claim 12, wherein the second frequency is varied over a plurality of different frequencies and the reference frequency is varied over the same plurality of different frequencies.

* * * * *